(12) United States Patent
Jollez et al.

(10) Patent No.: US 11,167,265 B2
(45) Date of Patent: *Nov. 9, 2021

(54) PROCESS AND APPARATUS FOR MANUFACTURING WATER-ABSORBING MATERIAL AND USE IN CAT LITTER

(71) Applicant: 7905122 Canada Inc., Boucherville (CA)

(72) Inventors: Paul Jollez, Sherbrooke (CA); Isabelle Bolduc, Saint-Hubert (CA)

(73) Assignee: 7905122 Canada Inc., Boucherville (CA)

( * ) Notice: Subject to any disclaimer, the term of this patent is extended or adjusted under 35 U.S.C. 154(b) by 40 days.

This patent is subject to a terminal disclaimer.

(21) Appl. No.: 16/712,474

(22) Filed: Dec. 12, 2019

(65) Prior Publication Data

US 2020/0188880 A1 Jun. 18, 2020

Related U.S. Application Data

(62) Division of application No. 15/516,171, filed as application No. PCT/CA2015/050984 on Sep. 30, 2015, now Pat. No. 10,583,420.

(Continued)

(51) Int. Cl.
*A01K 1/015* (2006.01)
*B01J 20/24* (2006.01)
(Continued)

(52) U.S. Cl.
CPC ......... *B01J 20/3212* (2013.01); *A01K 1/0152* (2013.01); *A01K 1/0155* (2013.01);
(Continued)

(58) Field of Classification Search
CPC .... B01J 20/24; B01J 20/262; B01J 20/28004; B01J 20/2803; B01J 20/28073;
(Continued)

(56) References Cited

U.S. PATENT DOCUMENTS 4,460,684 A 7/1984 Bauer
4,615,923 A 10/1986 Marx
(Continued)

FOREIGN PATENT DOCUMENTS

CA 2308537 11/2000
CA 2352502 1/2002
(Continued)

OTHER PUBLICATIONS

Office Action received in Japanese Application No. JP 2017-517668 dated Oct. 8, 2019 (including English Translation).
(Continued)

*Primary Examiner* — Benjamin L Lebron
(74) *Attorney, Agent, or Firm* — Avant Law Group, LLC

(57) ABSTRACT

A process for manufacturing particles of water-absorbing material is provided. The process includes providing a powder bed composed of an absorptive powder comprising a water-absorbing polysaccharide onto a surface; releasing an aqueous solution from a solution dispenser so as to contact the powder bed, thereby forming a solution-impregnated humid material; letting the solution-impregnated humid material agglomerate in substantially shear-less conditions to form an agglomerated humid material, the solution-impregnated humid material being supported by the surface; and drying the agglomerated humid material, thereby forming the particles.

20 Claims, 16 Drawing Sheets

Related U.S. Application Data

(60) Provisional application No. 62/210,148, filed on Aug. 26, 2015, provisional application No. 62/058,342, filed on Oct. 1, 2014.

(51) Int. Cl.
| | |
|---|---|
| *B01J 20/28* | (2006.01) |
| *B01J 20/30* | (2006.01) |
| *B01J 20/32* | (2006.01) |
| *C12Q 1/28* | (2006.01) |
| *C12Q 1/54* | (2006.01) |
| *B01J 20/26* | (2006.01) |
| *C08L 1/04* | (2006.01) |
| *C08L 3/02* | (2006.01) |
| *C08L 5/00* | (2006.01) |
| *C08L 5/14* | (2006.01) |

(52) U.S. Cl.
CPC ............. *B01J 20/24* (2013.01); *B01J 20/262* (2013.01); *B01J 20/2803* (2013.01); *B01J 20/28004* (2013.01); *B01J 20/28011* (2013.01); *B01J 20/28069* (2013.01); *B01J 20/28073* (2013.01); *B01J 20/28076* (2013.01); *B01J 20/3028* (2013.01); *B01J 20/3078* (2013.01); *B01J 20/321* (2013.01); *C08L 1/04* (2013.01); *C08L 3/02* (2013.01); *C08L 5/00* (2013.01); *C08L 5/14* (2013.01); *C12Q 1/28* (2013.01); *C12Y 111/01007* (2013.01); *A01K 1/0154* (2013.01); *B01J 20/26* (2013.01); *B01J 20/261* (2013.01); *B01J 2220/445* (2013.01); *B01J 2220/46* (2013.01); *B01J 2220/4825* (2013.01); *B01J 2220/49* (2013.01); *B01J 2220/68* (2013.01); *C12Q 1/54* (2013.01); *C12Y 101/03004* (2013.01); *G01N 2800/042* (2013.01)

(58) Field of Classification Search
CPC ................ B01J 20/28076; B01J 20/321; B01J 20/3212; B01J 20/34; B01J 20/261; B01J 20/3803; B01J 20/3028; B01J 20/3078; B01J 20/26; B01J 20/28011; B01J 20/28069; B01J 2220/46; B01J 2220/4825; B01J 2220/49; B01J 2220/445; C12Q 1/28; C12Q 1/54; A01K 1/0154; A01K 1/0155; A01K 1/0152; G01N 2800/042; C12Y 101/03004; C12Y 111/01007

See application file for complete search history.

(56) References Cited

U.S. PATENT DOCUMENTS

| | | |
|---|---|---|
| 4,883,021 A | 11/1989 | Ducharme |
| 5,735,232 A | 4/1998 | Lang |
| 5,760,121 A | 6/1998 | Beall |
| 6,019,062 A | 2/2000 | Lombard et al. |
| 6,039,004 A | 3/2000 | Goss |
| 6,042,839 A | 3/2000 | Lahanas |
| 6,197,849 B1 | 3/2001 | Michl |
| 6,228,903 B1 | 5/2001 | Beall |
| 6,261,640 B1 | 7/2001 | Pinnavaia |
| 6,271,297 B1 | 8/2001 | Ishida |
| 6,376,034 B1 | 4/2002 | Brander |
| 6,399,690 B2 | 6/2002 | Lan |
| 6,407,155 B1 | 6/2002 | Qian |
| 6,414,069 B1 | 7/2002 | Pinnavaia |
| 6,521,690 B1 | 2/2003 | Ross |
| 6,579,927 B1 | 6/2003 | Fischer |
| 6,586,500 B2 | 7/2003 | Bagrodia |
| 6,730,719 B2 | 5/2004 | Powell |
| 7,429,009 B2 | 9/2008 | Nagasawa et al. |
| 7,533,630 B2 | 5/2009 | Steckel |
| 9,547,000 B2 | 1/2017 | Gravel-Lacroix |
| 10,908,150 B2* | 2/2021 | Jollez .............. C12Y 111/01007 |
| 2002/0165305 A1 | 11/2002 | Knudson, Jr. et al. |
| 2002/0169246 A1 | 11/2002 | Barbee et al. |
| 2003/0060555 A1 | 3/2003 | Lorah et al. |
| 2003/0108497 A1 | 6/2003 | Chevalier |
| 2003/0134942 A1 | 7/2003 | Lee et al. |
| 2003/0170905 A1 | 9/2003 | Kamyshny |
| 2008/0022940 A1 | 1/2008 | Kirsch |
| 2009/0217882 A1 | 9/2009 | Jenkins |
| 2012/0202236 A1* | 8/2012 | Jollez .................. A01K 1/0154 435/28 |
| 2014/0000525 A1 | 1/2014 | Schumski et al. |

FOREIGN PATENT DOCUMENTS

| | | |
|---|---|---|
| CA | 2462053 | 9/2004 |
| CA | 2607676 | 5/2008 |
| CA | 2607753 | 5/2008 |
| CA | 2607758 | 5/2008 |
| CA | 2737489 | 11/2010 |
| EP | 1327435 | 7/2003 |
| GB | 1240884 | 7/1971 |
| JP | 2003160694 | 6/2003 |
| JP | 2010041966 | 2/2010 |
| WO | WO 199858533 | 12/1998 |
| WO | WO 2004043663 | 5/2004 |
| WO | WO 2010133001 | 11/2010 |

OTHER PUBLICATIONS

International Search Report received in PCT Application No. PCT/CA2015/050984 dated Dec. 3, 2015.

\* cited by examiner

PROCESS AND APPARATUS FOR MANUFACTURING WATER-ABSORBING MATERIAL AND USE IN CAT LITTER

RELATED APPLICATIONS

The present patent document is a divisional application of U.S. application Ser. No. 15/516,171, filed Mar. 31, 2017, which is a National Stage application of International Patent Application Serial No. PCT/CA2015/050984, filed Sep. 30, 2015, which claims the benefit of the filing date under 35 U.S.C. § 119(e) of Provisional U.S. Patent Application Ser. No. 62/058,342, filed Oct. 1, 2014 and Provisional U.S. Patent Application Ser. No. 62/210,148, filed Aug. 26, 2015, which are hereby incorporated by reference.

FIELD

The technical field relates to absorbent materials, and more specifically relates to a process and apparatus for manufacturing particles of water-absorbing material that can be used in cat litter for example.

BACKGROUND

Water-absorbent materials such as superabsorbent materials including polysaccharides and superabsorbent polymers can be employed in different fields. For example, superabsorbent materials can be used in pet litter, household articles, sealing materials, humectants for agricultural products for soil conditioning, oil-drilling, anti-condensation coatings, water-storing materials in agriculture/horticulture, absorbent paper products, bandages and surgical pads, disposable sanitary products (such as diapers, incontinence articles, feminine hygiene products, airlaids and absorbent dressings), wound dressings, or as chemical absorbents.

Among known water absorbent materials, polysaccharides and polysaccharide mixtures have been widely used, alone or in conjunction with inorganic absorbent materials such as phyllosilicates. The more widely used polysaccharides are typically based on starch and/or cellulose, and the phyllosilicates can for example include bentonite.

Many processes for manufacturing such absorbent materials are known, and include for example granulation. A widely-used granulation process is wet granulation, including for example high shear mixture granulation, fluid bed granulation, extrusion-spheronization and spray drying. Wet granulation is known to have many advantages, such as increasing the density of the material, providing a better distribution of a compound of interest within the material compared to some other methods, reducing dust hazards, preventing segregation of powders and increasing the hydrophilicity of otherwise hydrophobic materials.

However, wet granulation also has many disadvantages. For example, granulation can be costly, as it often requires qualified personnel, large operation space and special equipment. Wet granulation also typically has a high energy requirement. Loss of material can occur during various stages of processing, and incompatibilities between the formulation components are typically aggravated during processing. More specifically, high shear mixture granulation can sometimes lead to mechanical degradation of the material.

Fluid bed granulation and extrusion-spheronization are often labor-intensive and time consuming, and have various other challenges.

There is therefore still a need for a process and apparatus for manufacturing water-absorbing materials that overcome at least one of the above-mentioned issues.

SUMMARY

In some implementations, there is provided a process for manufacturing a water-absorbing material, including: providing an absorptive powder including a water-absorbing polysaccharide onto a surface, thereby obtaining a powder bed; releasing an aqueous solution from a solution dispenser so as to contact the powder bed, thereby forming a solution-impregnated humid material; maintaining the solution-impregnated humid material supported by the surface and in substantially shear-less conditions until the solution-impregnated humid material agglomerates to produce an agglomerated humid material; and drying the agglomerated humid material, thereby forming the water-absorbing material.

In some implementations, the surface is a substantially planar surface.

In some implementations, the process further includes displacing the solution-impregnated humid material away from the solution dispenser.

In some implementations, the powder bed is in translation relative to the solution dispenser.

In some implementations, releasing the aqueous solution includes pouring the aqueous solution under gravity onto the powder bed.

In some implementations, releasing the aqueous solution is performed from a distance of at most 10 cm above the powder bed.

In some implementations, releasing the aqueous solution is performed such that the aqueous solution has a velocity of at most 1.5 m/s upon contacting the powder bed.

In some implementations, the step of releasing the aqueous solution is performed such that a first portion of the absorptive powder is used to form the agglomerated humid material and a second portion of the absorptive powder remains as residual powder.

In some implementations, the process further includes separating the residual powder from the agglomerated humid material.

In some implementations, separating the residual powder from the agglomerated humid material includes sieving.

In some implementations, the process further includes recycling at least a portion of the residual powder for re-use as part of the powder bed.

In some implementations, the surface extends substantially horizontally.

In some implementations, the process further includes controlling a thickness of the powder bed.

In some implementations, the thickness is of about 1 cm to about 5 cm.

In some implementations, the absorptive powder further includes a second polysaccharide mixed with the water-absorbing polysaccharide.

In some implementations, the second polysaccharide includes a crystalline polysaccharide.

In some implementations, the crystalline polysaccharide includes cellulose, a cellulose derivative or a mixture thereof.

In some implementations, the cellulose includes microcrystalline cellulose (MCC), nanocrystalline cellulose (NCC) or a mixture thereof.

In some implementations, the water-absorbing polysaccharide includes a starch, a modified starch, a cellulose derivative, an alginate, an alginate derivative, a gelling polysaccharide or a mixture thereof.

In some implementations, the water-absorbing polysaccharide includes pregelatinized starch.

In some implementations, the particles of water-absorbing material have an effective porosity of about 0.5 mL/g to about 2.0 mL/g.

In some implementations, the effective porosity is of about 0.8 mL/g to about 1.2 m L/g.

In some implementations, the effective porosity is of about 0.9 mL/g to about 1.1 m L/g.

In some implementations, the particles of water-absorbing material are provided with pores having an equivalent diameter greater than about 20 µm.

In some implementations, the equivalent diameter is of about 20 µm to about 40 µm.

In some implementations, the equivalent diameter is of about 20 µm to about 30 µm.

In some implementations, the particles of water-absorbing material have a free swelling capacity greater than about 900%.

In some implementations, the particles of water-absorbing material have a free swelling capacity greater than about 1000%.

In some implementations, the drying includes drying under vacuum.

In some implementations, the drying includes drying by heating.

In some implementations, the drying is performed by heating to temperatures ranging from ambient temperature to about 65° C.

In some implementations, the particles of water-absorbing material have a density of about 0.20 g/cm$^3$ to about 0.39 g/cm$^3$.

In some implementations, the density is of about 0.25 g/cm$^3$ to about 0.35 g/cm$^3$.

In some implementations, the density is of about 0.30 g/cm$^3$ to about 0.35 g/cm$^3$.

In some implementations, the absorptive powder further includes at least one of magnesium stearate, celite, magnesium carbonate and talc.

In some implementations, the aqueous solution is released in the form of discrete drops onto the powder bed such that: the solution-impregnated humid material is produced in the form of solution-impregnated humid particles; the agglomerated humid material is produced in the form of agglomerated humid particles; and the water-absorbing material is produced in the form of particles of water-absorbing material.

In some implementations: the water-absorbing material is a chromogenic absorbent material for detecting a detectable substance in an animal excretion; and the aqueous solution is a chromogenic solution including: a trigger agent; and a chromogenic indicator oxidizable into a colored and/or fluorescent substance in the presence of the trigger agent and the detectable substance, and In some implementations: the detectable substance includes a peroxidase or a pseudoperoxidase; and the trigger agent includes an oxidizing agent responsive to peroxidatic/ pseudoperoxidatic activity in the animal excretion.

In some implementations, the detectable substance includes blood.

In some implementations, the oxidizing agent includes a hydroperoxide, a hydroperoxide precursor or a mixture thereof.

In some implementations: the detectable substance includes glucose; and the trigger agent includes a catalytic system including an oxido-reductase and a peroxidase or a pseudoperoxidase.

In some implementations, the oxido-reductase includes glucose oxidase.

In some implementations, the peroxidase includes horseradish peroxidase.

In some implementations, there is provided a system for manufacturing particles of water-absorbing material, including: a surface; a powder feeder configured to release an absorptive powder mixture onto the surface, thereby forming a powder bed; a solution dispenser for dripping discrete drops of an aqueous solution onto the powder bed, such that the drops are impregnated with respective amounts of the absorptive powder mixture, thereby forming solution-impregnated humid particles isolated from each other and supported by the surface; and a drying unit for drying the solution-impregnated humid particles, thereby forming the particles of water-absorbing material.

In some implementations, the surface is a substantially planar surface.

In some implementations, the surface is a conveying surface.

In some implementations, the conveying surface is configured to displace the solution-impregnated humid material away from the solution dispenser.

In some implementations, the conveying surface is configured to displace the powder bed in a translation movement relative to the solution dispenser.

In some implementations, the solution dispenser is configured to release the aqueous solution from a distance of at most 10 cm above the powder bed.

In some implementations, the solution dispenser is configured to release the aqueous solution such that the aqueous solution has a velocity of at most 1.5 m/s upon contacting the powder bed.

In some implementations, the solution dispenser releases the aqueous solution such that a first portion of the absorptive powder is used to form the agglomerated humid material and a second portion of the absorptive powder remains on the surface as residual powder.

In some implementations, the system further includes a first sieve located on or embedded in the conveying surface, for recycling of the residual powder.

In some implementations, the system further includes a second sieve located on or embedded in the conveying surface, for recovering the solution-impregnated humid particles.

In some implementations, there is provided a process for manufacturing particles of water-absorbing material, including:
  providing an absorptive powder including a water-absorbing polysaccharide onto a surface, thereby obtaining a powder bed;
  dripping an aqueous solution as discrete drops from a solution dispenser so as to contact the powder bed and become impregnated by the absorptive powder to form corresponding solution-impregnated humid particles;
  handling the solution-impregnated humid particles to remain isolated from each other until the solution-impregnated humid particles agglomerate, thereby forming respective agglomerated humid particles; and
  drying the stable humid particles to produce the particles of water-absorbing material.

In some implementations, the powder bed and the aqueous solution are contacted such that the solution-impregnated humid material remains in spaced relation with respect to the surface.

In some implementations, the powder bed and the aqueous solution are contacted such that substantially all of the aqueous solution remains in the solution-impregnated humid particle.

In some implementations, there is provided a process for manufacturing particles of water-absorbing material, including:
- providing an absorptive powder including a water-absorbing polysaccharide onto a surface, thereby obtaining a powder bed;
- releasing an aqueous solution in the form of discrete drops from a solution dispenser so as to contact the powder bed, thereby forming solution-impregnated humid particles;
- maintaining the solution-impregnated humid particles supported by the surface and in substantially shear-less conditions until the solution-impregnated humid particles agglomerate to produce agglomerated humid particles; and
- drying the agglomerated humid particles, thereby forming the particles of water-absorbing material.

In some implementations, there is provided a process for manufacturing particles of chromogenic absorbent material for an animal litter, the process including:
- providing an absorptive powder including a water-absorbing polysaccharide onto a surface, thereby obtaining a powder bed;
- providing a chromogenic solution by addition of a chromogenic agent and an oxidizing agent or by addition of the chromogenic agent and a first catalytic compound, into a solvent;
- releasing the chromogenic solution in the form of discrete drops from a solution dispenser so as to contact the powder bed, thereby forming a solution-impregnated humid material;
- maintaining the solution-impregnated humid material supported by the surface and in substantially shear-less conditions until the solution-impregnated humid material agglomerates to produce agglomerated humid particles; and
- drying the agglomerated humid particles, thereby forming the particles of chromogenic absorbent material.

In some implementations, the aqueous solution comprises a colorimetric pH indicator and the water-absorbing material is a chromogenic absorbent material for measuring the pH of a substance contacting the water-absorbing material.

In some implementations, the pH indicator includes methyl violet, thymol blue, benzyl orange, bromophenol blue, congo red, methyl orange, methyl red, bromocresol purple, bromothymol blue, phenol red, cresol red, thymol blue, phenolphthalein, tymolphthalein, alizarin yellow R or combinations thereof.

In some implementations, the pH indicator includes a Bogen universal indicator.

In some implementations, there is provided a chromogenic absorbent material for an animal litter, comprising:
- a chromogenic indicator comprising a pH indicator for determining the pH of an animal excretion; and
- an absorptive material which is porous, for absorbing the animal excretion, the absorptive material comprising:
  - a water-absorbing polysaccharide providing absorptive properties to the chromogenic absorbent material; and
  - a second polysaccharide providing structural integrity to the chromogenic absorbent material.

In some implementations, the second polysaccharide comprises a crystalline polysaccharide.

In some implementations, the crystalline polysaccharide comprises cellulose, a cellulose derivative or mixtures thereof.

In some implementations, the cellulose comprises microcrystalline cellulose (MCC), nanocrystalline cellulose (NCC), or a mixture thereof.

In some implementations, the absorptive material comprises:
- about 35 wt. % to about 65 wt. % of the water-absorbing polysaccharide; and
- about 35 wt. % to about 65 wt. % of the second polysaccharide.

In some implementations, the absorptive material comprises:
- about 45 wt. % to about 55 wt. % of the water-absorbing polysaccharide; and
- about 45 wt. % to about 55 wt. % of the second polysaccharide.

In some implementations, there is provided a chromogenic absorbent material for an animal litter, comprising:
- a chromogenic indicator comprising a pH indicator for determining the pH of an animal excretion; and
- an absorptive material which is porous, for absorbing the animal excretion, the absorptive material comprising a water-absorbing polysaccharide, wherein the chromogenic absorbent material has a density of about 0.20 $g/cm^3$ to about 0.39 $g/cm^3$.

In some implementations, the density of the chromogenic absorbent material is about 0.25 $g/cm^3$ to about 0.35 $g/cm^3$.

In some implementations, the density of the chromogenic absorbent material is about 0.30 $g/cm^3$ to about 0.35 $g/cm^3$.

In some implementations, there is provided a chromogenic absorbent material for an animal litter, comprising:
- a chromogenic indicator comprising a pH indicator for determining the pH of an animal excretion; and
- an absorptive material which is porous, for absorbing the animal excretion, the absorptive material comprising a water-absorbing polysaccharide, wherein the chromogenic absorbent material is a porous material having an effective porosity of about 0.5 mL/g to about 2.0 mL/g.

In some implementations, the effective porosity is of about 0.6 mL/g to about 1.5 m L/g.

In some implementations, the effective porosity is of about 0.8 mL/g to about 1.2 m L/g.

In some implementations, the effective porosity is of about 0.9 mL/g to about 1.1 m L/g.

In some implementations, the chromogenic absorbent material is provided with pores having an equivalent diameter greater than about 20 μm.

In some implementations, the chromogenic absorbent material is provided with pores having an equivalent diameter of about 20 μm to about 40 μm.

In some implementations, the chromogenic absorbent material is provided with pores having an equivalent diameter of about 20 μm to about 30 μm.

In some implementations, the material has a free swelling capacity greater than about 900%.

In some implementations, the material has a free swelling capacity greater than about 1000%.

In some implementations, there is provided a chromogenic absorbent material for an animal litter, comprising:

a chromogenic indicator comprising a pH indicator for determining the pH of an animal excretion; and
an absorptive material which is porous, for absorbing the animal excretion, the absorptive material comprising:
a water-absorbing polysaccharide providing absorptive properties to the chromogenic absorbent material; and
a superabsorbent polymer (SAP).

In some implementations, the absorptive material comprises up to about 3 wt. % of the SAP.

In some implementations, the absorptive material comprises about 1 wt. % to about 3 wt. % of the SAP.

In some implementations, the absorptive material comprises about 1 wt. % to about 2 wt. % of the SAP.

In some implementations, the SAP comprises at least one of a poly(acrylic acid) and a poly(methacrylic acid), or a salt thereof.

In some implementations, there is provided a chromogenic absorbent material for an animal litter, comprising:
a chromogenic indicator comprising a pH indicator for determining the pH of an animal excretion; and
an absorptive material which is porous, for absorbing the animal excretion, the absorptive material comprising:
a water-absorbing polysaccharide providing absorptive properties to the chromogenic absorbent material; and
a second polysaccharide providing structural integrity to the chromogenic absorbent material,
wherein the chromogenic absorbent material is a porous material having:
an effective porosity of about 20% to about 40%; and
a density of about 0.20 g/cm$^3$ to about 0.39 g/cm$^3$.

In some implementations, the water-absorbing polysaccharide comprises a starch, a modified starch, a cellulose derivative or a gelling polysaccharide, or a mixture thereof.

In some implementations, the water-absorbing polysaccharide comprises pregelatinized starch.

In some implementations, the cellulose derivative comprises a cellulose ester or a cellulose ether, or a mixture thereof.

In some implementations, the cellulose derivative comprises carboxymethyl cellulose (CMC).

In some implementations, the gelling polysaccharide comprises agar-agar, guar or xanthan, or a mixture thereof.

In some implementations, the chromogenic indicator is distributed within the absorptive material.

In some implementations, the pH indicator includes methyl violet, thymol blue, benzyl orange, bromophenol blue, congo red, methyl orange, methyl red, bromocresol purple, bromothymol blue, phenol red, cresol red, thymol blue, phenolphthalein, tymolphthalein, alizarin yellow R or combinations thereof.

In some implementations, the pH indicator includes a Bogen universal indicator.

Use of the chromogenic absorbent material as defined herein as chromogenic particles in combination with animal litter.

In some implementations, the animal litter comprises clay based particles, cellulosic particles, perlite based particles, silica based particles, corn based particles, paper based particles or wheat based particles or a combination thereof.

In some implementations, the clay based particles comprise montmorillonite.

In some implementations, the clay based particles comprise bentonite.

In some implementations, there is provided the use of the chromogenic absorbent material as described herein for measuring the pH in animal excretions.

In some implementations, the chromogenic particles are substantially evenly distributed on a top surface of the animal litter.

In some implementations, the chromogenic particles are substantially evenly distributed within the animal litter.

In some implementations, the chromogenic particles comprise pellets, granules, disks, squares according to their process of manufacture.

DETAILED DESCRIPTION

Figure 1:
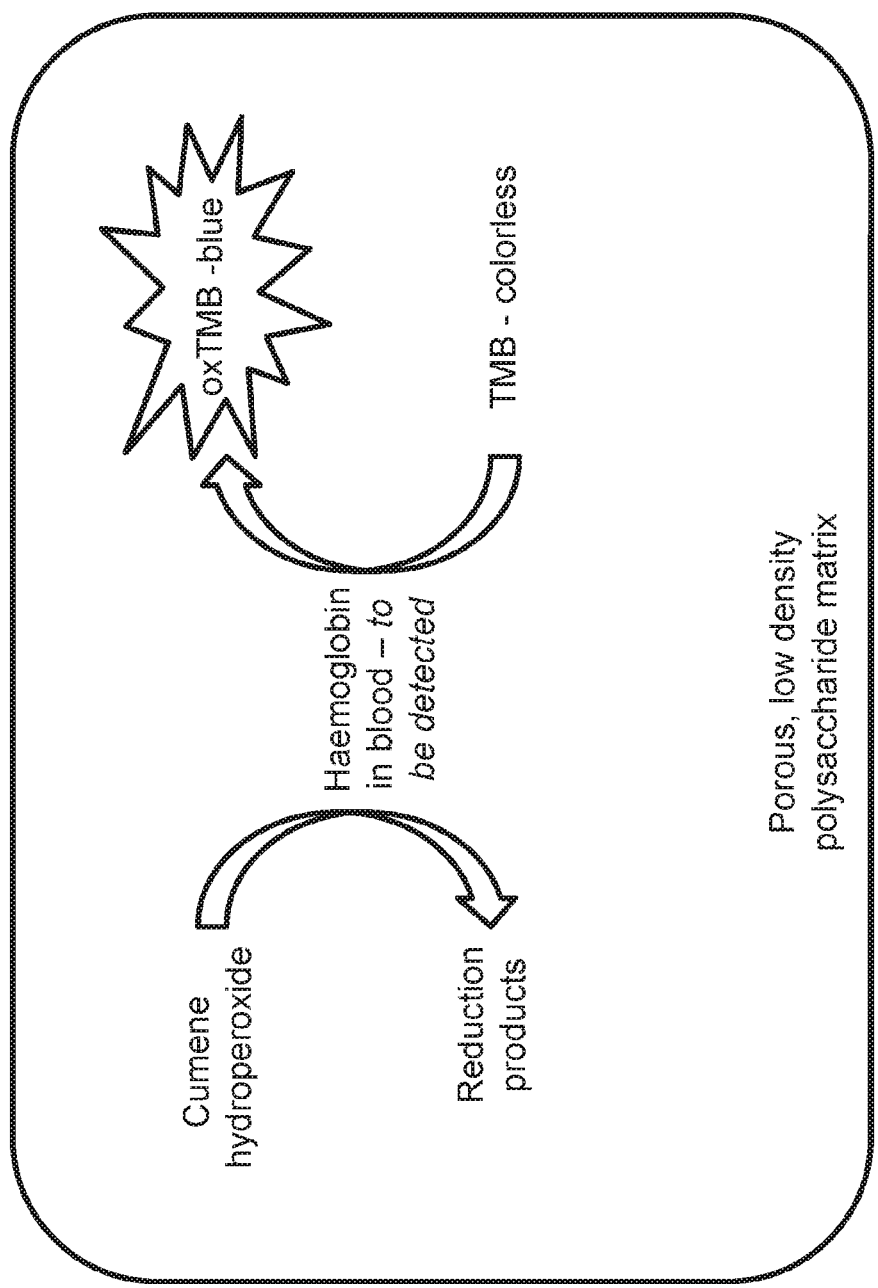
FIG. 1 is a scheme of the reaction pathway taking place in the particles of chromogenic absorbent material for the detection of blood in animal excretions.

The techniques described herein relate to a process and system for manufacturing a water-absorbing material.

The process includes providing an absorptive powder including a water-absorbing polysaccharide onto a surface, thereby obtaining a powder bed; releasing an aqueous solution from a solution dispenser so as to contact the powder bed, thereby forming a solution-impregnated humid material; maintaining the solution-impregnated humid material supported by the surface and in substantially shear-less conditions until the solution-impregnated humid material agglomerates to produce an agglomerated humid material; and drying the agglomerated humid material, thereby forming the water-absorbing material.

It should be understood that the term "water-absorbing material" generally refers to a material which can absorb and retain aqueous liquids (i.e., water-containing liquids). The water-absorbing material can include saccharides, polysaccharides, synthetic absorbent polymers, clays, or combinations thereof. In some implementations, the water-absorbing material is produced in the form of particles of water-absorbing material.

Further, some implementations described herein include a process for manufacturing particles of chromogenic water-absorbing material for detecting diseases related to the presence of blood in animal excretions, such as urinary tract disease, hemorrhage or cancer, or diseases related to higher-than-normal levels of glucose in the animal excretions, such as diabetes.

It should be understood that the term "particles" refers to discrete pieces of material of various shapes obtained by the manufacturing process. Optionally, the particles may generally have a circular cross-section with an average diameter ranging from 2.5 mm to 10 mm. Optionally, the particles include granules.

Some implementations of the process and system are described in greater detail below.

Process for Manufacturing Particles of Water-Absorbing Material

As described herein, the water-absorbing material can be produced in the form of particles of water-absorbing material. However, it will be understood that the water-absorbing material can also be produced in other forms such as two-dimensional or one-dimensional structures. A non-limitative example of a two-dimensional structure includes a continuous sheet of water-absorbing material, optionally having a length and width of at least several cm and a thickness between 2.5 mm and 10 mm. a non-limitative example of a one-dimensional structure includes generally elongated structures such as an elongated cylinder, optionally having a length of at least several cm and a diameter between 2.5 mm and 10 mm. It should also be noted that the one-dimensional and two-dimensional structures can optionally be cut or grinded to obtain particles of water-absorbing material.

The composition of the absorptive powder and/or of the aqueous solution is chosen depending on the application and use of the particles of water-absorbing material, or to obtain certain desirable physical-chemical properties. For example, by controlling the operating parameters of the process, the composition of the absorptive powder and/or the composition of the aqueous solution, the particles of water-absorbing material can have a lower density and/or higher porosity than other absorbing particles manufactured by known processes such as wet granulation or extrusion. Further, some compositions of the absorptive powder allow for the solution-impregnated humid material to agglomerate more easily, for example without the need of mixing the solution-impregnated humid material or subjecting the solution-impregnated humid material to shear, after contact with the aqueous solution.

The process for manufacturing particles of water-absorbing material includes providing an absorptive powder onto a surface, thereby forming a powder bed. The absorptive powder can include at least one of the water-absorbing components of the water-absorbing material, for example a polysaccharide or other water-absorbing compounds in powder form or a mixture of several polysaccharides or other water-absorbing compounds in powder form.

The surface can be any suitable two-dimensional structure onto which the absorptive powder can be disposed. The surface can be curved or substantially planar. In some implementations, the surface is a substantially planar surface which can be horizontal or inclined. It is understood that by "substantially planar", it is meant that the surface is generally flat and in a plane, although there can be minor surface roughness to the surface. For example the substantially planar surface can include a table top, a working surface of a laboratory bench, a working surface of a fume-hood, or a top surface of a conveyor belt or other types of conveyors. It is understood that the surface may be immobile or mobile. A mobile surface may be in motion continuously or during certain time periods only. In some implementations, the powder bed is provided on the surface with a thickness D between about 0.5 cm and about 5 cm, or between 1 cm and 2 cm.

The process also includes releasing an aqueous solution from a solution dispenser so as to contact the powder bed, thereby forming a solution-impregnated humid material. It is understood that the solution-impregnated humid material corresponds to the amount of absorptive powder of the powder bed which has been contacted with the aqueous solution, and which has not yet been agglomerated into agglomerated humid material or agglomerated humid particles.

It is understood that the expression "aqueous solution" refers to a solution in which the solvent includes water. For example, and without being limitative, the aqueous solution can include water and other water-miscible solvents such as acetone, ethanol, methanol and/or isopropanol. For example, the aqueous solution can include mixtures of water and acetone, water and ethanol or water and isopropanol. It is also understood that the aqueous solution can include other compounds, such as chemically active compounds or pharmaceutically active compounds. In some implementations, the solvent includes at least 50 wt % water. In some implementations, the other compounds can include a chromogenic indicator and/or an oxidizing agent, as will be described in further detail below.

In some implementations, releasing the aqueous solution includes pouring the aqueous solution under gravity onto the powder bed. Pouring the aqueous solution can be performed, for example, by pouring a continuous flow of aqueous solution onto the powder bed, spraying the aqueous solution onto the powder bed (i.e., under pressure), or by dripping the aqueous solution in the form of discrete drops. For example, when pouring the aqueous solution includes dripping the aqueous solution in the form of discrete drops onto the powder bed, the agglomerated humid material is produced in the form of agglomerated humid particles.

The aqueous solution can be released onto the powder bed from a distance. The distance is selected to be sufficient enough to enable penetration of the aqueous solution into the powder bed without substantially displacing the powder bed. In the case that the aqueous solution is released by dripping the aqueous solution in the form of discrete drops, the distance can be selected such that an impact between the drops and the powder bed minimizes bursting of the drops and minimizes production of micro-drops which can contaminate the powder bed. For example, in some implementations this distance may be of at most 10 cm above the powder bed, for example between 5 cm and 10 cm above the powder bed, or such that the aqueous solution has a velocity of at most 1.5 m/s, or between 1 m/s and 1.5 m/s, upon contacting the powder bed.

Optionally, dripping the aqueous solution can be performed so that each drop of the aqueous solution contacts the powder bed at a different location. Optionally, dripping the aqueous solution can be performed so that each drop of the aqueous solution contacting the powder bed forms a corresponding solution-impregnated humid particle. In some implementations, the process includes handling the solution-impregnated humid particles to remain isolated from each other until the solution-impregnated humid particles agglomerate, thereby forming respective agglomerated humid particles.

In some implementations, the process includes maintaining the solution-impregnated humid material supported by the surface and in substantially shear-less conditions until the solution-impregnated humid material agglomerates to produce an agglomerated humid material. In other words, after contact of the powder bed with the aqueous solution, the solution-impregnated humid material is kept in contact with the surface and in substantially shear-less conditions (or very low shear conditions) until an agglomerated material is produced. It is understood that the solution-impregnated humid material being "supported by the surface" or "kept in contact with the surface" means that the solution-impregnated humid material can either be directly supported by (or in direct contact with) the surface or indirectly supported by the surface through an underlying part of the powder bed which has not been contacted with the aqueous solution.

In some implementations, the powder bed is provided with a thickness D which prevents the solution from going through the powder bed and come into direct contact with the surface. In other words, the powder bed and the solution can be contacted such that the solution-impregnated humid material remains in spaced relation with respect to the surface—in such case, it is understood that the solution-impregnated humid material is indirectly supported by the surface through the underlying part of the powder bed, as explained herein. It is also understood that the material supported by the surface can be substantially immobile relative to the surface or can be moving relative to the surface.

It is understood that by "substantially shear-less" or "very low shear" conditions, it is meant that the solution-impregnated humid material is not subjected to shearing forces strong enough to cause a mechanical deformation of the solution-impregnated humid material. For example, the absorptive powder and the aqueous solution are not mechanically mixed or extruded. It is also understood that the shearing forces caused by optional conveying of the solution-impregnated humid material on a conveyor belt or other types of conveyors is considered to be negligible, such that the displacement of the solution-impregnated humid material on a conveyor during agglomeration is considered within the scope of the expression "substantially shear-less conditions".

It is understood that the term "agglomeration" (or corresponding verb "to agglomerate") refer to the aggregation of the solution-impregnated humid material in order to gather, form or crystallize into a ball, mass, cluster or a larger aggregate (i.e., grains or granules). The agglomeration is caused by the wetting of the powder bed by the aqueous solution (also referred to as an agglomeration liquid) and subsequent adhesion of particles of wetted powder (i.e, the solution-impregnated humid material) together in order to form the ball, mass, cluster or larger aggregate (i.e., the agglomerated humid material). The agglomeration of the solution-impregnated humid material to produce the agglomerated humid material can take an agglomeration period between 1 second and several minutes (e.g., 2 or 3 minutes), or between several seconds (e.g., 5 or 10 seconds) and 1 minute, depending on the composition of the absorptive powder and the aqueous solution. It is understood that during the agglomeration period, the solution-impregnated humid material can be displaced on the surface or kept substantially immobile relative to the surface.

The process also includes drying the agglomerated humid material, thereby forming the particles of water-absorbing material. In some implementations, the drying is performed under vacuum. In some implementations, the drying is performed by heating at temperatures ranging from ambient temperature to about 65° C. The drying can for example be performed in a drying oven or a rotary evaporator.

Optionally, the process can further include displacing the solution-impregnated humid material away from the solution dispenser, for example on a conveyor belt. The solution-impregnated humid material can be in translation relative to the solution dispenser. Typically, the powder bed passes below the solution dispenser, but other configurations are possible.

Optionally, the aqueous solution can be released to contact part of the absorptive powder to form the agglomerated humid material, while another part of the absorptive powder can remain as residual powder. The residual powder can be separated from the agglomerated humid material, for example by sieving, and at least a portion of the residual powder can be recycled to form part of the powder bed.

The composition of the absorptive powder is selected such that the agglomeration can take place in substantially shear-less conditions, as explained herein. To such end, the absorptive powder includes a water-absorbing polysaccharide. The water-absorbing polysaccharide provides absorptive properties to the water-absorbing material. In some implementations, the water-absorbing polysaccharide may be a starch, a modified starch, amylopectin, amylose, modified amylose, a cellulose derivative, an alginate, an alginate derivative, a gelling polysaccharide or a mixture thereof. Non-limiting examples of starches and modified starches are starch granules, pregelatinized starch, waxy starches, anionic starches, cationic starches, fractionated starches, cross-linked starches or mixtures thereof. Such starches may be obtained from many sources, including but not limited to wheat, maize, buckwheat, potato, cassaya, sorghum, millet, oat, arrowroot, barley, beans, peas, rice, rye, and mixtures thereof. Non-limiting examples of cellulose derivatives are cellulose esters and cellulose ethers, or a mixture thereof. A non-limiting example of a cellulose ether is carboxymethyl cellulose (CMC). Non-limiting examples of gelling polysaccharides are agar-agar, guar and xanthan, or a mixture thereof.

Optionally, the water-absorbing polysaccharide can be a glass-like polysaccharide. Glass-like polysaccharides are substantially amorphous polysaccharides and include glass-like characteristics. Glass-like polysaccharides substantially lack an organized crystalline pattern. Glass-like polysaccharides are typically prepared by melting or heating the polysaccharide to a temperature above its glass-transition temperature, followed by cooling to a temperature below its glass transition or melting point temperature. A non-limiting example of a glass-like polysaccharide, which has been found to be particularly suitable to be included in some implementations of the absorptive powder is pregelatinized starch.

Optionally, the absorptive material further includes a superabsorbent polymer (SAP). Optionally, the absorptive material includes in weight up to about 3 wt. %, or between 1 wt. % and 2.5 wt. % of the SAP. Non-limiting examples of SAP are poly(acrylic acids) and poly(methacrylic acids), salts thereof, or mixtures thereof. A non-limiting example of SAP is sodium polyacrylate, which is an efficient SAP. It should be understood that other types of SAPs may be used, such as superabsorbent starches or other synthetic superabsorbent polymers.

In an optional aspect, each particle of water-absorbing material further includes a second polysaccharide providing structural integrity. By "providing structural integrity", it is meant that the second polysaccharide reduces or prevents the breaking up of the particles of water-absorbing material upon handling or upon contact an aqueous liquid. In other words, the second polysaccharide reduces the brittleness of the water-absorbing material while preventing an increase of the softness or pliability of the water-absorbing material. In some scenarios, the second polysaccharide provides sufficient structural integrity so that the particles of the water-absorbing material cannot be easily broken or fractured by hand and are relatively unpliable and rigid. For example, when the absorptive material consists of 100 wt % pregelatinized starch, the particles of water-absorbing material can tend to be soft and pliable and thus not as easily manipulated.

Optionally, the second polysaccharide includes a crystalline polysaccharide. Examples of crystalline polysaccharides are cellulose, cellulose derivatives or mixtures thereof. In an optional aspect, the cellulose includes microcrystalline cellulose (MCC), nanocrystalline cellulose (NCC) or a mixture thereof. In an optional aspect, the absorptive material includes in weight: about 35% to about 65% or about 45% to 55% of the water-absorbing polysaccharide, and about 35% to about 65% or about 45% to about 55% of the second polysaccharide. In an optional aspect, the crystalline polysaccharide is less water-absorbent than the water-absorbing polysaccharide. When the absorptive powder includes more than one constituent, the process further includes mixing together the constituents (for example, the water-absorbing polysaccharide and the second polysaccharide), in order to form the absorptive powder.

In some implementations, depending on the composition of the absorptive powder, the particles of water-absorbing material may have a density of about 0.20 g/cm$^3$ to about 0.39 g/cm$^3$, of about 0.20 g/cm$^3$ to about 0.35 g/cm$^3$, of about 0.25 g/cm$^3$ to about 0.35 g/cm$^3$, or of about 0.30 g/cm$^3$ to about 0.35 g/cm$^3$.

In some implementations, depending on the composition of the absorptive powder, the chromogenic absorbent material may have a total porosity of about 65% to about 85%, or of about 70% to about 80%. It is understood that the total porosity refers to the fraction of the bulk material volume (V) which is not occupied by solid matter. If the volume of solids is denoted by Vs, and the pore volume as Vpore=V−Vs, the total porosity can be expressed as shown in Equation 1 below.

$$\text{total porosity} = \phi = \frac{V - Vs}{V} = \frac{Vpore}{V} \text{ (mL/mL)} \qquad \text{Equation 1}$$

The total porosity may for example be measured by: placing a known volume of particles of water-absorbing material into a container; covering the particles with a liquid; and measuring the volume of liquid needed to cover the particles (Vc). The total porosity is then expressed as the ratio of the volume of added liquid (Vc) to the volume of particles (V).

In some implementations, depending on the composition of the absorptive powder, the particles of water-absorbing material have an effective porosity of about 0.5 mL/g to about 2.0 mL/g, of about 0.6 mL/g to about 1.5 mL/g, of about 0.8 mL/g to about 1.2 mL/g or of about 0.9 mL/g to about 1.1 mL/g. It is understood that the effective porosity (also referred to as connected porosity or true porosity) is defined as the ratio of the connected pore volume to the total bulk volume. The effective porosity may for example be measured by: placing a known mass (m) of particles of water-absorbing material into a container; covering the particles with a liquid; measuring the volume of liquid needed to cover the particles (Vc); removing the soaked particles from the container; measuring the liquid remaining in the container (Vr); and calculating the volume of liquid absorbed in the chromogenic absorbent particles (Va=Vc−Vr). The effective porosity may then be obtained as shown in Equation 2 below.

$$\text{effective porosity} = \phi_e = \frac{Vc - Vr}{m} = \frac{Va}{m} \text{ (ml/g)} \qquad \text{Equation 2}$$

It is to be noted that the effective porosity may also be expressed as the ratio Va/V in ml/ml.

In some implementations, the particles of water-absorbing material have a free swelling capacity (FSC) greater than about 900%, or greater than about 1000%. The FSC is one type of measurement used for measuring the absorption properties of a material. An FSC measurement is performed by soaking the material to be tested in a liquid to be absorbed (in the present case, water) for a given time and weighing the material after the liquid has been absorbed.

In some implementations, the particles of water-absorbing material have a hardness which is sufficient to withstand the weight of an animal (e.g. a cat or a dog) standing on the particles (i.e. a part of the animal's weight is applied onto the particle). In some implementations, the force required for compressing spheroidal particles of water-absorbing material having a mass between 22 mg and 38 mg by 1 mm is between about 15 N and about 90 N. It should be understood that the "hardness" of a particle of water-absorbing material refers to the ability of the particle to be deformed by applying a compression force onto the particle, without the particle breaking or disaggregating. It should also be understood that in some implementations, depending on the composition of the particles of water-absorbing material and conditions of agglomeration, less than about 20% of the particles break or are disaggregated after a compression of more than 1.1 mm.

System for Manufacturing Particles of Water-Absorbing Material

Figure 10:
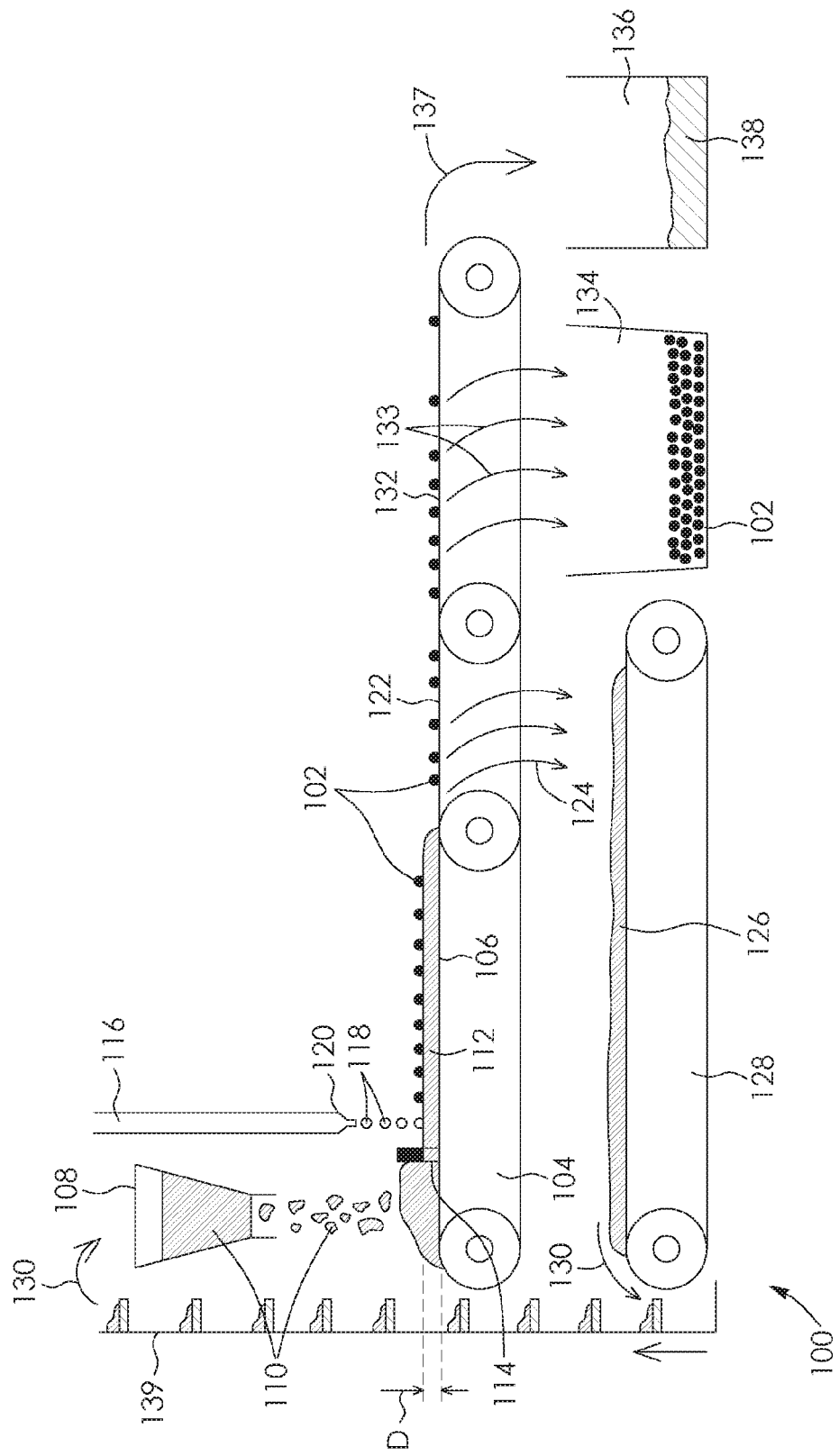
FIG. 10 shows a schematic representation of an apparatus used for the manufacturing of particles of water-absorbing material.

Now referring to FIG. 10, there is provided a system for manufacturing the particles of water-absorbing material. The system includes an apparatus 100 for forming the agglomerated humid material 102 and a dryer (not shown) for drying the agglomerated humid material and forming the particles of water-absorbing material. The apparatus 100 also includes a conveyor 104 including a conveying surface 106, which is in this case a substantially planar surface. In some implementations, the conveying surface 106 can be operated such that the particles of agglomerated humid material 102 are displaced at a speed between about 0.1 m/min to about 6 m/min, or between about 1.2 m/min to about 6 m/min.

The apparatus 100 also includes a powder feeder 108 located at a first end of the conveyor 104. The powder feeder 108 is used for disposing absorptive powder 110 onto the conveying surface 106, thereby forming a powder bed 112. In some implementations, the powder feeder 108 has a loading capacity of up to about 30 L of the absorptive powder 110.

In some implementations, the apparatus 100 can include a thickness controlling unit 114 for controlling a thickness D of the powder bed 112. The thickness controlling unit 114 can be located proximate to the powder feeder 108 and can optionally include a blade located above the conveying surface 106. In some implementations, the thickness controlling unit 114 is configured so that the thickness of the powder bed is between 0.5 cm and 5 cm, or between 1 cm and 2 cm.

The apparatus 100 also includes a solution supply (not shown) connected to a solution delivery unit 116. The solution delivery unit 116 is configured for releasing the aqueous solution onto the powder bed 112. Typically, the powder bed 112 passes below the solution delivery unit 116, but other configurations are possible. In some implementations, the solution delivery unit 116 is configured for dripping discrete drops 118 of the aqueous solution onto the powder bed 112, such that the drops 118 are impregnated with respective amounts of the absorptive powder, thereby forming the solution-impregnated humid material which agglomerates to form the agglomerated humid material 102. In other implementations, the solution delivery unit 116 is configured for spraying the aqueous solution onto the powder bed 112 or for pouring the aqueous solution onto the powder bed 112 in a sheet-like manner.

In some implementations, the solution delivery unit 116 includes at least one solution outlet 120 located at a height above the conveying surface 110. For example, solution outlet 120 can be located between 5 cm and 10 cm above the conveying surface 106. In some implementations, the solution delivery unit 118 includes a plurality of solution outlets 120 spaced from each other. Optionally, the solution outlets 120 span across the width of the conveying surface 106. For example, the solution delivery unit 116 can include ten solution outlets 120 spaced from each other by about 2 cm to 4 cm.

Still referring to FIG. 10, in some implementations, the apparatus 100 can include a first sieve 122 (i.e., a powder sieve) located on or embedded in the conveying surface 106, for retrieving 124 at least part of residual absorptive powder 126. The residual absorptive powder 126 is the remaining absorptive powder 110 which was not contacted by the aqueous solution released from the solution delivering system 116. Optionally, the apparatus 100 can further include a second conveyor 128 or a powder recycling bin (not shown) located under the first sieve 122, for receiving the residual absorptive powder 126. The residual absorptive powder received on the second conveyor 128 or in the powder recycling bin can be recycled back 130 to the powder feeder 108 and reused as absorptive powder 110. In some implementations, the residual absorptive powder 126 can be conveyed back to the powder feeder 108 using a vertical conveyer 139. In some implementations, the residual absorptive powder 126 can be manually recovered from the powder recycling bin and into the powder feeder 108. In some implementations, the apparatus 100 can include a second sieve 132 (i.e., a particle sieve) located on or embedded in the conveying surface 106, for recovering 133 the agglomerated humid material 102. Optionally, the apparatus 100 can further include an agglomerated humid material recovery bin 134 located under the second sieve 132, for receiving the agglomerated humid material 102. In some implementations, the apparatus 100 can include a waste material recovery bin 136, for recovering 137 waste material 138 which was not sieved by the first and second sieves 122, 132. In some implementations, the perforations of the first sieve 122 are of about 3.5 mm to about 4 mm. In some implementations, the perforations of the second sieve 132 are of about 4.5 mm to about 5 mm.

It is understood that the length of the conveying surface 106 and the speed at which the conveying surface is displaced can vary depending on the time required for the agglomerated humid material to be formed. The length of the conveying surface 106 and the displacement speed of the conveying surface 106 can therefore be adapted such that the agglomerated humid particles are recovered 133 shortly after they are formed. In some scenarios, optimizing the length and displacement speed of the conveying surface 106 can allow for reduced energy consumption of the system.

Particles of Chromogenic Absorbent Material for Use in Animal Litter and Process for Manufacturing the Same The process described herein can for example be used for manufacturing additives to be used in or in conjunction with an animal litter. This exemplary application more specifically relates to a process of manufacturing a chromogenic water-absorbing material which may be used for detecting diseases or abnormalities in excretions. (also referred to herein as a "chromogenic absorbent material") for detecting diseases such as urinary tract disease, hemorrhage, cancer or diabetes in animal excretions.

In some implementations, the chromogenic absorbent material includes a chromogenic indicator and an absorptive powder (as described herein and also referred to herein as an "absorptive material"). In some implementations, the chromogenic absorbent material further includes an oxidizing agent. The chromogenic absorbent material can allow detecting disease features when contacted with excretions and/or abnormalities in the excretions. In some implementations, the chromogenic absorbent material is provided for detecting blood in excretions. In some implementations, the chromogenic absorbent material is provided for detecting glucose in excretions. In some implementations, the chromogenic absorbent material is provided for measuring the pH of excretions. In some implementations, the chromogenic absorbent material may be used in connection with an animal litter.

It should be understood that excretion refers to any matter excreted by an animal, such as urine or fecal matter. The chromogenic absorbent material may be used in any domestic animal litter including cat litter, dog litter and rodent litter. It may also be used for horse litter, cow litter or any other livestock litter. However, various implementations of the chromogenic absorbent material are not limited to detecting blood or glucose in animal excretions, or measuring the pH of animal excretions, and may be used to detect blood or glucose in human excretions, or for measuring the pH of human excretions, for example.

Particles of the chromogenic absorbent material may be dispersed within the animal litter or at the surface of the animal litter. In some implementations, the particles of the chromogenic absorbent material have a density which is lower than the density of the particles of the animal litter, such that the particles of the chromogenic absorbent material migrate to the surface of the animal litter when the animal litter is shaken. The animal litter may include clay based particles, cellulosic particles, perlite based particles, silica based particles, corn based particles, paper based particles, wheat based particles or other organic-based litter particles, or a combination thereof. For example and without being limitative, clay based particles may include bentonite and/or montmorillonite.

In some implementations, the particles of chromogenic absorbent material include: an oxidizing agent responsive to peroxidatic/pseudoperoxidatic activity in an excretion to provide oxidizing activity, or a first catalytic compound generating the oxidizing agent in situ; a chromogenic indicator being chromogenically responsive to the oxidizing activity of the oxidizing agent; and an absorptive material for absorbing the excretion, the absorptive material including a water-absorbing polysaccharide providing absorptive properties to the chromogenic absorbent material.

It should be understood that the expression "peroxidatic activity" refers to the ability of catalytic compounds to drive the reaction between hydroperoxides and colorless chromogenic electron donors which become fluorescent or visibly colored after oxidation.

It should be understood that the expression "pseudoperoxidatic activity" refers to the ability of a peroxidase or a non-peroxidase catalytic compound to drive the reaction between hydroperoxidases and colorless chromogenic electron donors which become fluorescent or visibly colored after oxidation. Certain transition metals and their ions and hemoproteins are known to have pseudoperoxidatic activity. Basophils, neutrophils, eosinophils and mast cells synthesize endogenous peroxidase which can be visualized at the ultrastructural level in the secretory apparatus of immature cells. Red blood cells and hematin containing compounds have iron as part of their heme groups, which can catalyze the oxidation of chromogenic electron donors. This pseudoperoxidatic activity can be inhibited with strong $H_2O_2$ solutions, sodium azide and methanol-$H_2O_2$ solutions.

The oxidizing agent is reactive to peroxidatic/pseudoperoxidatic activity and is able to oxidize the chromogenic indicator in the presence of a peroxidase or a pseudoperoxidase. For example, the peroxidase can be horseradish peroxidase. For example, the pseudoperoxidase can be haemoglobin present in blood. In an optional aspect, the oxidizing agent includes a hydroperoxide.

It should be understood that "hydroperoxide" refers to compounds of the general formula ROOH, wherein the R group is an aryl, alkyl or acyl group (organic hydroperoxide), or a hydrogen atom (hydrogen peroxide). For example and without being limitative, the hydroperoxide can be cumene hydroperoxide (CHP), diisopropylbenzene dihydroperoxide or hydrogen peroxide, or a mixture thereof. Hydroperoxides are suitable for the detection of peroxidatic/pseudoperoxidatic activity.

In some implementations, the oxidizing agent may be a hydroperoxide precursor such as sodium percarbonate. Sodium percarbonate is a chemical adduct of sodium carbonate and hydrogen peroxide. The formula of sodium percarbonate is $2Na_2CO_3 \cdot 3H_2O_2$. Sodium percarbonate decomposes to sodium carbonate and hydrogen peroxide, for example upon contact with water.

In some implementations, the oxidizing agent is not initially added to the chromogenic absorbent material, but is generated in situ by a first catalytic compound present in the chromogenic absorbent material. It should be understood that "generated in situ" means that the oxidizing agent is directly synthesized in the chromogenic absorbent material from a precursor. For example, the first catalytic compound may be an enzyme such as an oxido-reductase. For example, the first catalytic compound may be glucose oxidase (GOx). Optionally, the precursor may be oxygen ($O_2$), which can be reduced to hydrogen peroxide in the presence of glucose oxidase. In an optional aspect, the reduction of the precursor to the oxidizing agent can take place in the presence of a saccharide or polysaccharide which can be oxidized by the first catalytic compound.

In some implementations, the oxidizing activity of the oxidizing agent is triggered by the presence of peroxidatic/pseudoperoxidatic activity in excretions. The oxidizing agent therefore oxidizes the chromogenic indicator which then changes of color. More particularly, the chromogenic indicator is an electron donor, i.e. a reducing agent that changes color upon losing an electron.

In some implementations, the chromogenic indicator is a benzidine-type compound, i.e. a compound as shown in formula I:

Formula I

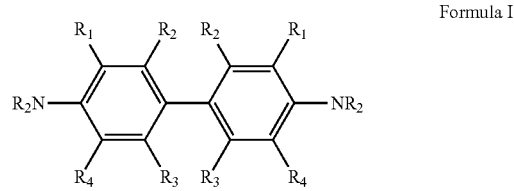

In Formula I, groups $R_1$, $R_2$, $R_3$ and $R_4$ may be the same or different and may be hydrogen, halogen, a lower alkyl or alkoxy group containing 1 to 4 carbon atoms, a ($C_1$-$C_4$)-dialkylamino group, an acetylamino group, a nitro group or an aromatic group which may be substituted.

Optionally, the chromogenic indicator may be a compound as shown in Formula II:

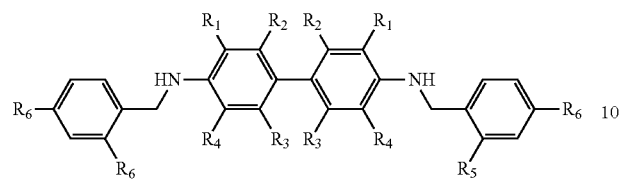

Formula II

In Formula II, groups $R_1$, $R_2$, $R_3$ and $R_4$ may be the same or different and represent hydrogen, halogen, and a lower alkyl or alkoxy group containing 1 to 4 carbon atoms, a ($C_1$-$C_4$)-dialkylamino group, an acetylamino group, a nitro group or an aromatic group which may be substituted; $R_5$ and $R_6$ are the same or different and represent water-soluble groups as hydroxyl group amino group, acidic group, disulfonyl group, ether group, halogen, and a lower alkyl or alkoxy group containing 1 to 4 carbon atoms, a ($C_1$-$C_4$)-dialkylamino group, an acetylamino group or a nitro group.

Thus, a water soluble benzidine-type chromogenic indicator of Formula II, responds in the presence of hydroperoxide and peroxidase by changing its light absorptive capability, which is due to the chemical transformation to the compound shown in Formula III:

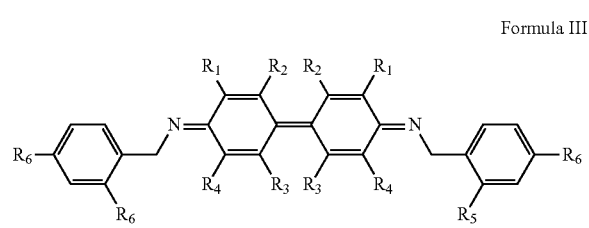

Formula III

It is understood that several different types of benzidine chromogenic indicators may be used.

Optionally, the chromogenic indicator may be 3,3',5,5'-tetramethylbenzidine (TMB). TMB is a colorless agent which turns blue upon oxidation. The peroxidase and/or pseudo-peroxidase catalyze the oxidation of TMB by the oxidizing agent (hydroperoxide) according to the following oxidation reaction.

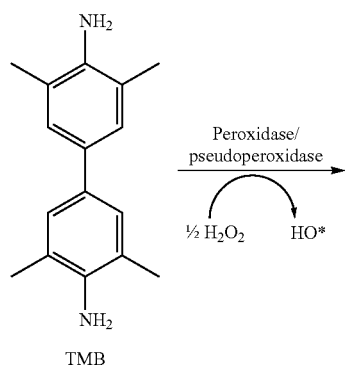

TMB

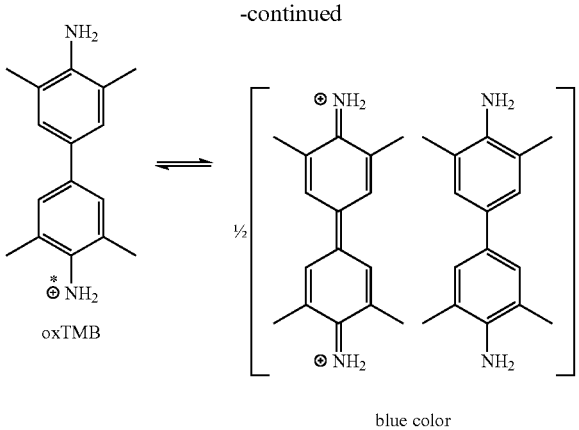

oxTMB blue color

In some implementations, the chromogenic absorbent material may turn blue upon contact with excretions containing at least traces of blood (with therefore peroxidase/pseudo-peroxidase activity).

It should be understood that "blue" refers to any shade of blue. The chromogenic absorbent material may need a contact time with excretions sufficient to enable coloration. In an optional aspect, the particles may turn blue after a contact time ranging from about 10 seconds to about 30 min, or from about 10 seconds to about 1 min, depending on the nature of the absorptive material.

In some implementations, the chromogenic absorbent material may turn to different shades of blue depending on the blood or glucose concentration in excretions. The intensity of the blue shade may be proportional to the blood concentration or glucose concentration in excretions.

In some implementations, the chromogenic absorbent material may include an odor-retardant agent. For example, the odor-retardant agent may be N-(n-butyl) thiophosphoric triamide (n-BTPT), having the molecular formula $C_4H_{14}N_3PS$ with the following structure:

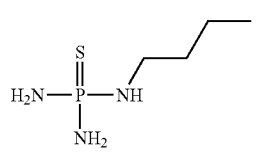

In some implementations, the chromogenic composition may further include a colour enhancer. Optionally, it may also include a buffering agent, a stabilizer, a metal scavenger agent or a combination thereof. The colour enhancer may optionally be 6-methoxyquinoline, lepidin, phenol derivatives, nitrobenzene, N-methylpyrrolidone, ethylene carbonate or any combination thereof. The buffering agent may optionally include citrate, sodium citrate, phosphate, acetate or any combination thereof. In some implementations, the buffering agent is used for maintaining the pH of the solution at about 5. The stabilizer may optionally be ascorbic acid, ammonium molybdate and derivatives thereof, polyethylene glycol, polyvinylpyrrolidone, polyethylene oxide and derivatives thereof, dibutylhydroxytoluene (BHT), or combination thereof. The metal-scavenger agent may optionally be EDTA, EDTA sodium salt or any combination thereof.

In some implementations, a chromogenic absorbent material is provided for detecting a detectable substance in an animal excretion. The chromogenic absorbent material includes:

a trigger agent responsive to the presence of the detectable substance;

a chromogenic indicator convertable into a chromogenically active substance in the presence of the trigger agent and the detectable substance; and an absorptive material for absorbing the animal excretion, the absorptive material being porous and including:

a water-absorbing polysaccharide providing absorptive properties to the chromogenic absorbent material; and a second polysaccharide providing structural integrity to the chromogenic absorbent material.

It is understood that the trigger agent may be selected depending on the detectable substance and such that the conversion of the chromogenic indicator takes place and/or is catalyzed only if both the trigger agent and the detectable substance are present. For example, when the detectable substance is a peroxidase or a pseudoperoxidase, the trigger agent may be an oxidizing agent responsive to peroxidatic/pseudoperoxidatic activity in the animal excretion and the conversion of the chromogenic indicator includes oxidation into the chromogenically active substance.

In some implementations, the detectable substance includes a pseudoperoxidase (such as blood which includes haemoglobin), and the trigger agent is a hydroperoxide (such as cumene hydroperoxide) or a hydroperoxide precursor.

In some implementations, the detectable substance is glucose, and the trigger agent is a catalytic system including an oxido-reductase and a peroxidase, or an oxido-reductase and a pseudoperoxidase. For example, the oxido-reductase may be glucose oxidase and the peroxidase may be horseradish peroxidase.

Figure 9:
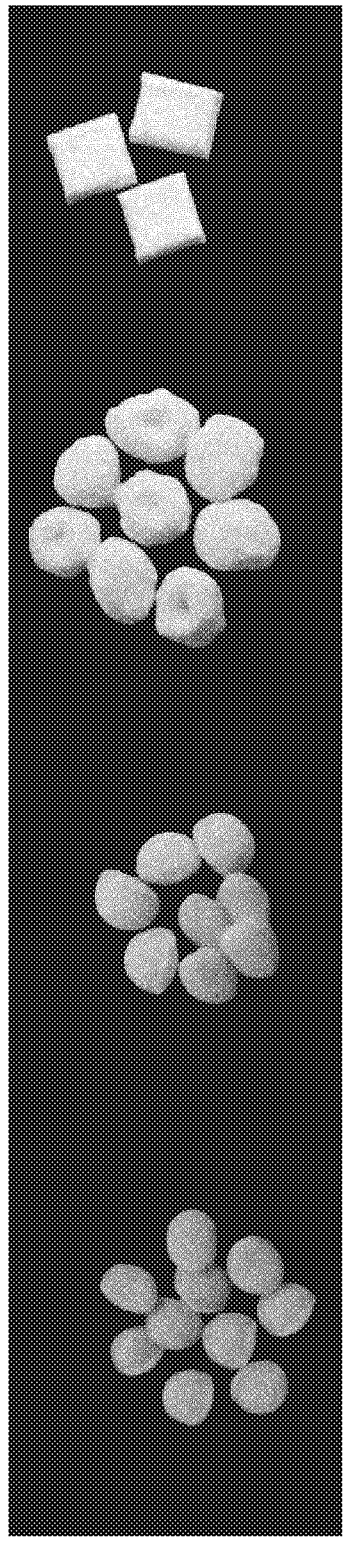
FIG. 9 shows photographs of extruded starch particles (9A, comparative), extruded starch particles in which gas was injected during extrusion (9B, comparative), particles of chromogenic absorbent material in which the absorptive material includes 50% PGS and 50% MCC (9C), and particles of pressed cellulose (9D, comparative).

Now referring to FIG. 9, a photograph showing different particles is shown. Particles 9A are extruded starch particles obtained under high shear, without injection of gas during extrusion. Particles 9A were made as a comparative example. Particles 9B are extruded starch particles obtained under high shear, with injection of gas during extrusion, Particles 9B were made as a comparative example. Particles 9D are pressed cellulose pulp particles and were also made as a comparative example. Particles 9C are chromogenic absorbent particles in which the absorptive material includes 50% pregelatinized starch (PGS) and 50% microcrystalline cellulose (MCC). Particles 9C were obtained through an implementation of the process as described herein and correspond to sample 25 as detailed in Example 2.

As can be seen in FIG. 9, particles 9A and 9B are in the form of compact pellets and particles 9D are in the form of pressed, compact squares. Particles 9C of chromogenic absorbent material (i.e. particles of water-absorbing material) are in the form of granules having a concave shape on one side and a convex shape on an opposite side.

Scanning electron micrographs of the particles of FIG. 9 were obtained in order to compare the morphology of particles 9A, 9B, 9C and 9D. Scanning electron micrographs showing the surface of the particles are shown in FIGS. 6A to 6D. Scanning electron micrographs showing cross sections of the particles are shown in FIGS. 7A to 7C and 8A to 8C. The scanning electron microscope used was a MEB JEOL JSM-5900LV™ (low vacuum).

Figure 6B:
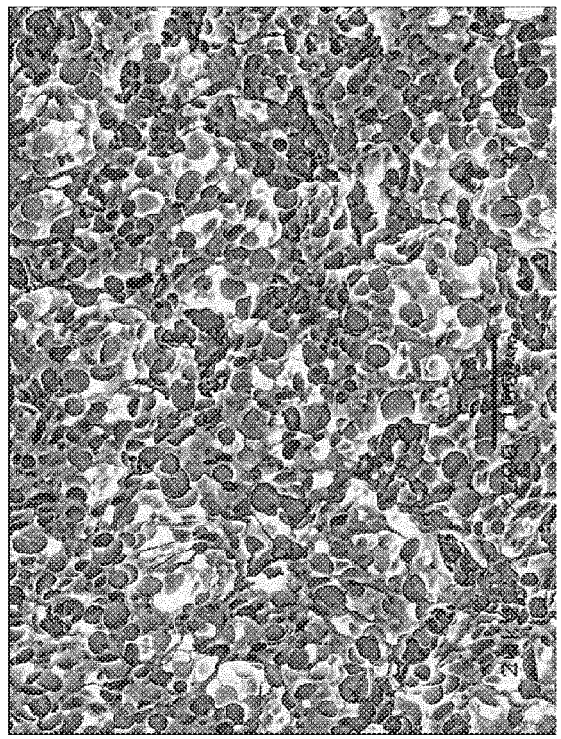
FIG. 6B is a ×200 scanning electron micrograph showing the surface of an extruded starch particle in which gas was injected during extrusion (comparative figure).
Figure 6A:
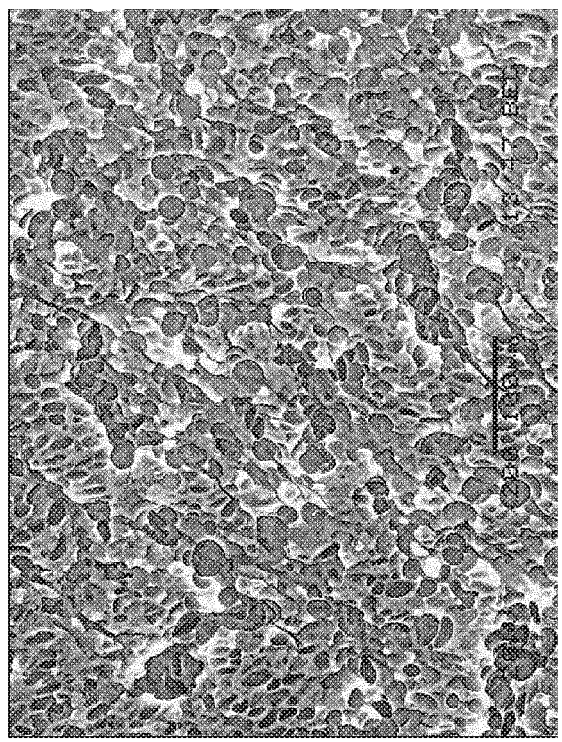
FIG. 6A is a ×200 scanning electron micrograph showing the surface of an extruded starch particle (comparative Figure).

FIGS. 6A and 6B (comparative) show the surface of extruded starch particles obtained under high shear, with and without injected gas during extrusion. As can be seen, the surface of the extruded starch includes microscopic starch globules having a size of between about 5 μm and about 30 μm.

Figure 6D:
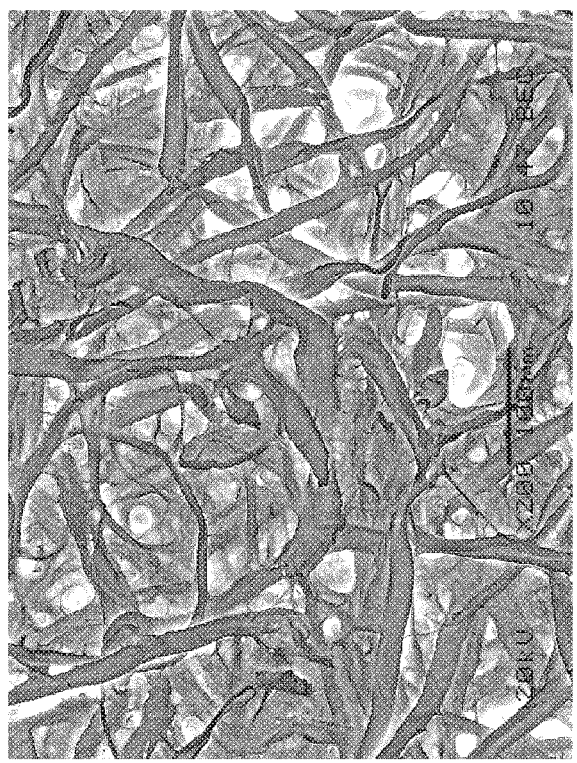
FIG. 6D is a ×200 scanning electron micrograph showing the surface of a particle of pressed cellulose (comparative figure).

FIG. 6D (comparative) shows the surface of pressed cellulose pulp particles. Elongated cellulose fibers can be seen on the surface. The fibers have a length of between about 100 μm and about 400 μm, and a width of between about 10 μm to about 30 μm.

Figure 6C:
FIG. 6C is a ×200 scanning electron micrograph showing the surface of a particle of chromogenic absorbent material in which the absorptive material includes 50% PGS and 50% MCC.

FIG. 6C shows the surface of chromogenic absorbent particles manufactured using an implementation of the process described herein, and in which the absorptive material includes 50% pregelatinized starch (PGS) and 50% microcrystalline cellulose (MCC). Microsructures of various shapes can be seen on the micrograph. The microsructures have a length of between about 10 μm to about 100 μm, and a width of between about 10 μm to about 100 μm.

Different microstructure morphologies are apparent for the different particles. The particles of FIGS. 6A and 6B mainly include a smooth globular microstructure, the particles of FIG. 6D mainly includes generally smooth filamentous microstructure, while the particles of FIG. 6C mainly include a rough, irregular, block-shaped microstructure.

The pore structure of the particles was also studied. Cross sections of the particles of chromogenic absorbent material were observed by scanning electron microscopy, as can be seen in FIG. 7C, and as detailed in Example 6. The cross sections were obtained by freeze-fracture under liquid nitrogen and observed by SEM to determine the pore density and equivalent diameter of the pores. It is understood that "pore density" refers to the proportion of the surface which is not covered by solid material (i.e., the ratio of the pore surface to the total surface). It is also understood that "equivalent diameter" refers to the approximate diameter of a comparable circular cylinder having the same volume as that of the pore.

Depending of the absorptive material, the particles of chromogenic absorbent material may have a pore density greater than about 20%, or greater than about 25%, or of about 27% to about 33%, for example. The pores of the particles of chromogenic absorbent material have an equivalent diameter greater than about 20 μm, or of about 20 μm to about 40 μm, or of about 20 μm to about 30 μm.

Figure 7A:
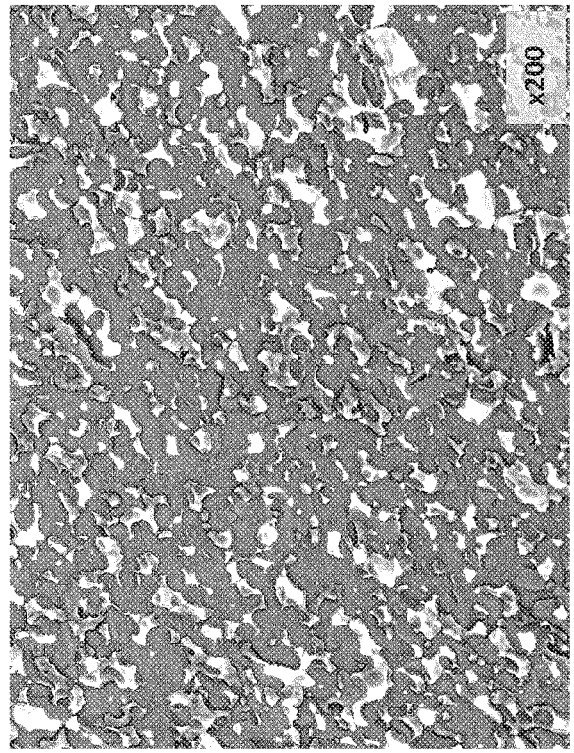
FIG. 7A is a ×200 scanning electron micrograph showing a cross section of an extruded starch particle, obtained by freeze-fracture (comparative Figure).
Figure 7B:
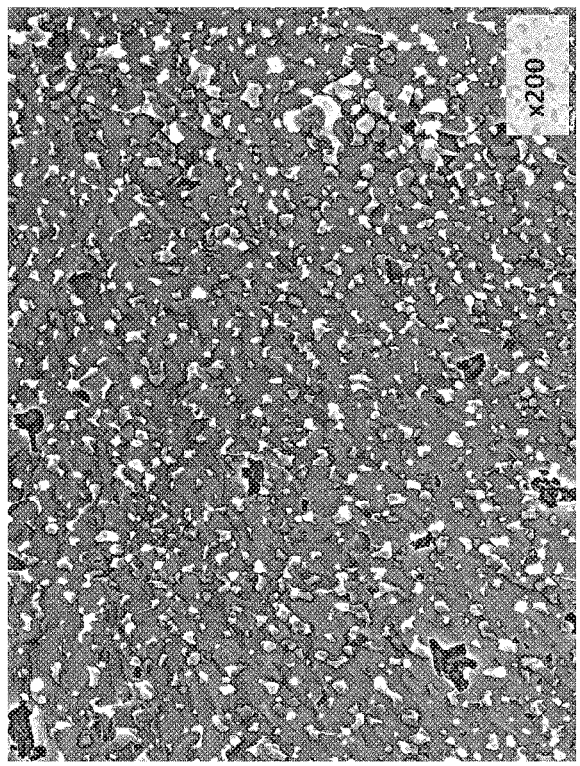
FIG. 7B is a ×200 scanning electron micrograph showing a cross section of an extruded starch particle in which gas was injected during extrusion. The cross section is obtained by freeze-fracture (comparative figure).
Figure 7C:
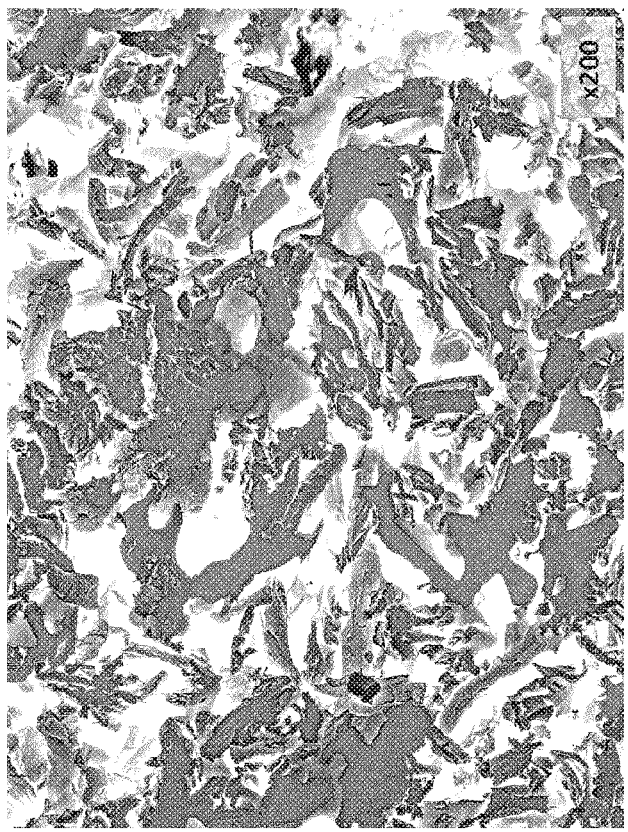
FIG. 7C is a ×200 scanning electron micrograph showing a cross section of a particle of chromogenic absorbent material in which the absorptive material includes 50% PGS and 50% MCC.
Figure 8B:
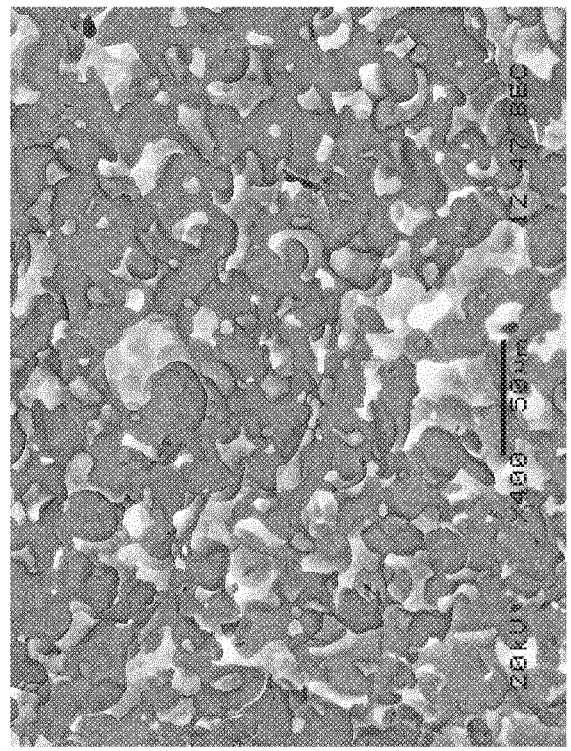
FIG. 8B is a ×400 scanning electron micrograph showing a cross section of an extruded starch particle in which gas was injected during extrusion. The cross section is obtained by freeze-fracture (comparative figure).
Figure 8A:
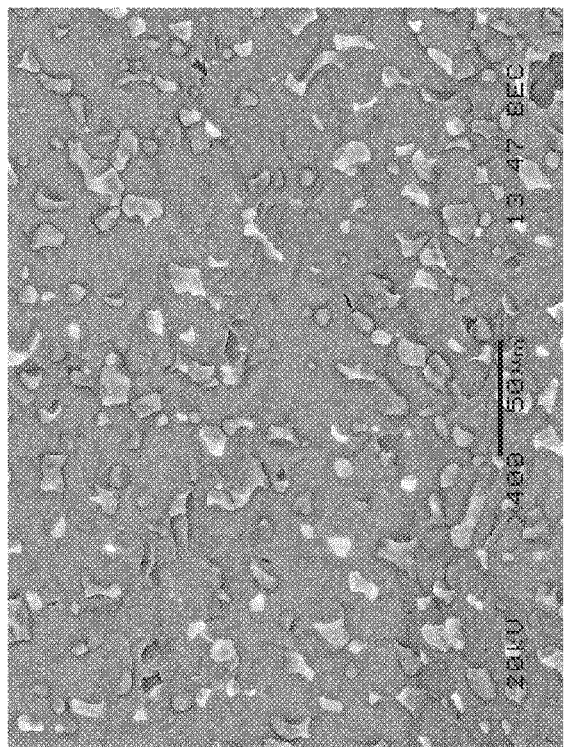
FIG. 8A is a ×400 scanning electron micrograph showing a cross section of an extruded starch particle, obtained by freeze-fracture (comparative Figure).
Figure 8C:
FIG. 8C is a ×400 scanning electron micrograph showing a cross section of a particle of chromogenic absorbent material in which the absorptive material includes 50% PGS and 50% MCC.

Cross sections of extruded starch particles were also examined as a comparative example (see also Example 6), and can be seen in FIGS. 7A and 7B.

Now referring to FIG. 1, an example of chromogenic absorbent material for detecting blood in animal excretions is described. The substance to be detected (blood) includes haemoglobin which is a pseudoperoxidase. In the absence of blood (i.e., in the absence of peroxidase and/or pseudoperoxidase), the reduction of cumene hydroperoxide (the oxidizing agent) into reduction products and the oxidation of TMB into oxidized TMB (oxTMB) is not catalyzed. When traces of blood are present (i.e., when traces of haemoglobin are present), the reactions are enabled and TMB is oxidized into oxTMB which has a distinctive blue color. The chromogenic absorbent material may be obtained to include a porous polysaccharide matrix having a low density. Thus, the chromogenic absorbent material described is suited for the detection of blood in animal excretions, and therefore for detection of urinary tract diseases for example.

Figure 2:
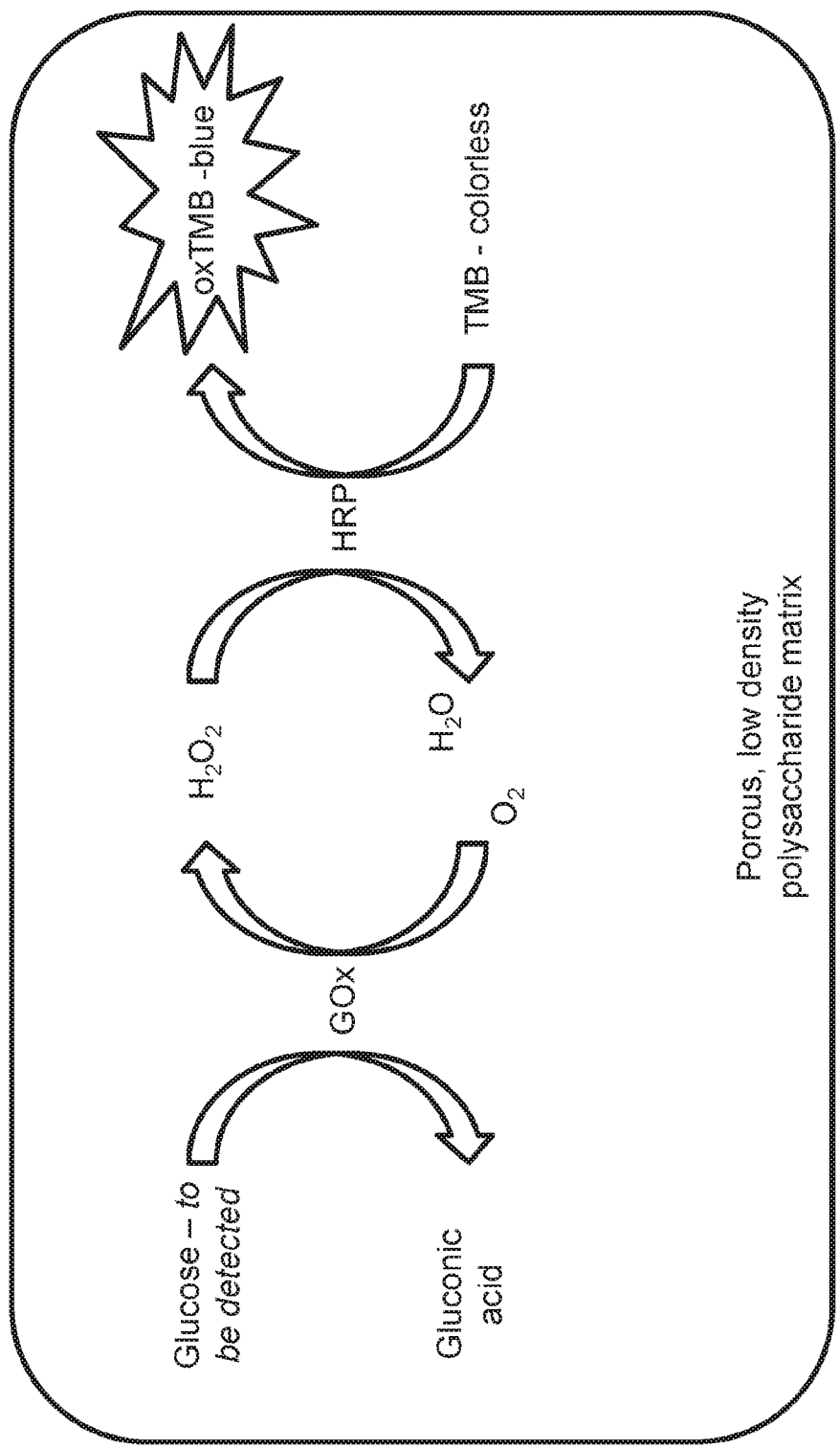
FIG. 2 is a scheme of the reaction pathway taking place in the particles of chromogenic absorbent material for the detection of glucose in animal excretions.

Now referring to FIG. 2, an example of the chromogenic absorbent material for detecting glucose in animal excretions is described. The chromogenic absorbent material used for detecting glucose includes a first catalytic compound (such as glucose oxidase) to generate hydrogen peroxide in situ. In the case of glucose detection, the chromogenic absorbent material further includes a second catalytic compound for catalyzing the oxidation of TMB and the reduction of the hydroperoxide. The second catalytic compound may be horseradish peroxidase. It is understood that other peroxidases or pseudoperoxidases may be used in other implementations. It should also be understood that in the case of glucose detection, the polysaccharide matrix does not include polysaccharides which may react with the first catalytic compound. If such polysaccharides were used, hydrogen peroxide would be generated in situ even without the presence of glucose in the animal excretions, which would lead to false positive test results. For example, when the first catalytic compound is glucose oxidase, the absorptive material does not include starches or modified starches that could react and give false positives.

Still referring to FIG. 2, when glucose is not present in the animal excretions, TMB is not oxidized, as no hydrogen peroxide is generated in situ. When glucose is present in the animal excretions, glucose oxidase oxidizes the glucose into gluconic acid and reduces oxygen into hydrogen peroxide. The horseradish peroxidase then reduces the hydrogen peroxide into water and oxidizes TMB into oxTMB which has a distinctive blue color. The chromogenic absorbent material described in FIG. 2 may be obtained to include a porous polysaccharide matrix having a low density, and is suited for detection of glucose in animal excretions, and therefore for detection of diabetes in animals for example.

In some implementations, the absorptive powder mixture used for making chromogenic particles for detecting glucose can include an oxidizing agent which is not responsive to peroxidatic/pseudoperoxidatic activity in the excretion. Such oxidizing agent can include potassium iodate, potassium bromate, or mixtures thereof. In some implementations, 0.1 wt % to 1 wt % oxidizing agent can be present in the absorptive powder mixture (for example 0.5 wt % oxidizing agent). In some implementations, the particles of chromogenic absorbent material include: a chromogenic indicator which is a pH indicator for colorimetric determination of the pH; and an absorptive material for absorbing the excretion, the absorptive material including a water-absorbing polysaccharide providing absorptive properties to the chromogenic absorbent material. The pH indicator can include any known colorimetric pH indicator, such as (and without being limitative) methyl violet, thymol blue, benzyl orange, bromophenol blue, congo red, methyl orange, methyl red, bromocresol purple, bromothymol blue, phenol red, cresol red, thymol blue, phenolphthalein, tymolphthalein, alizarin yellow R or combinations thereof. For example, the pH indicator can include a universal pH indicator such as Bogen universal indicator solution which includes bromothymol blue (as a sodium salt), phenolphthalein and methyl red.

In some implementations, the chromogenic indicator may be homogeneously dispersed throughout the absorptive material according to the preparation method of the chromogenic absorbent material. The chromogenic indicator may be present not only at the exterior surface of a given particle, but also in a neighboring sub-surface region that can be rapidly exposed to excretions that are absorbed into the particle. Additionally, when the absorptive material is glassy or substantially transparent, the presence of the chromogenic indicator in a sub-surface region allows it to be readily visible when a color change occurs and also avoids exposure to the air. In addition, the absorptive material may be provided with certain absorptive properties relative to the environment when in operation. For instance, the absorptive material may be provided to enable faster absorption of excretions compared to the surrounding material, such as surrounding animal litter, to facilitate adequate exposure of the excretions to the active agents in the chromogenic absorptive material. As different animal litters may have different absorptive properties, the absorptive material may be provided in accordance with pre-determined litter absorption properties, e.g. according to a maximum litter absorption rate. For instance, in some implementations, the absorptive material has a higher absorption rate compared to the litter material, and optionally a substantially higher absorption rate. For example, the absorptive material may have an absorption rate about 3 to 10 times higher, or about 5 to 10 times higher than the absorption rate of the litter material.

In some implementations, the process described herein can be used for manufacturing the chromogenic absorbent material.

In some implementations, the process includes:
providing an absorptive powder including a water-absorbing polysaccharide onto a surface, thereby obtaining a powder bed;
preparing a chromogenic solution by addition of a chromogenic agent, into a solvent;
releasing the chromogenic solution from a solution dispenser so as to contact the powder bed, thereby forming a solution-impregnated humid material;
maintaining the solution-impregnated humid material supported by the surface and in substantially shear-less conditions until the solution-impregnated humid material agglomerates to produce an agglomerated humid material; and
drying the agglomerated humid material, thereby forming the chromogenic absorbent material.

In some implementations, the process includes:
providing an absorptive powder including a water-absorbing polysaccharide onto a surface, thereby obtaining a powder bed;
providing a chromogenic solution including a solvent and a chromogenic agent;
releasing the chromogenic solution from a solution dispenser so as to contact the powder bed, thereby forming a solution-impregnated humid material;
maintaining the solution-impregnated humid material supported by the surface and in substantially shear-less conditions until the solution-impregnated humid material agglomerates to produce an agglomerated humid material; and
drying the agglomerated humid material, thereby forming the chromogenic absorbent material.

In some implementations, the process includes:
providing an absorptive powder including a water-absorbing polysaccharide onto a surface, thereby obtaining a powder bed;
preparing a chromogenic solution by addition of a chromogenic agent and an oxidizing agent or by addition of the chromogenic agent and a first catalytic compound, into a solvent;
releasing the chromogenic solution from a solution dispenser so as to contact the powder bed, thereby forming a solution-impregnated humid material;
maintaining the solution-impregnated humid material supported by the surface and in substantially shear-less conditions until the solution-impregnated humid material agglomerates to produce an agglomerated humid material; and
drying the agglomerated humid material, thereby forming the chromogenic absorbent material.

In some implementations, the process includes:
providing an absorptive powder including a water-absorbing polysaccharide onto a surface, thereby obtaining a powder bed;

providing a chromogenic solution including:
   a solvent; and
      a chromogenic agent and an oxidizing agent, or a chromogenic agent and a first catalytic compound;
   releasing the chromogenic solution from a solution dispenser so as to contact the powder bed, thereby forming a solution-impregnated humid material;
   maintaining the solution-impregnated humid material supported by the surface and in substantially shear-less conditions until the solution-impregnated humid material agglomerates to produce an agglomerated humid material; and
   drying the agglomerated humid material, thereby forming the chromogenic absorbent material.

In some implementations, the aqueous solution is released in the form of discrete drops onto the powder bed such that the agglomerated humid material is produced in the form of agglomerated humid particles and the chromogenic absorbent material is produced in the form of particles of chromogenic absorbent material.

In some implementations wherein the absorptive powder includes at least a second polysaccharide, the process can further include mixing together the water-absorbing polysaccharide, the second polysaccharide and any further optional component such as a superabsorbent polymer.

The chromogenic solution includes the chromogenic agent and can further include the oxidizing agent or a first catalytic compound for generating the oxidizing agent in situ. In the case of chromogenic solutions used for making particles of chromogenic absorbent material for the detection of glucose in an excretion, the chromogenic solution further includes a second catalytic compound. For example, the second catalytic compound includes a peroxidase, a pseudoperoxidase, or a mixture thereof. In the case of a chromogenic solution used for measuring the pH of an excretion, the chromogenic solution includes a pH indicator (or a combination of pH indicators).

Optionally, the chromogenic solution may include a buffering agent so as to maintain a pH of the chromogenic solution between 5 and 7. Extreme pH may be avoided.

Optionally, the chromogenic solution may include a colour enhancer, a stabilizer, a metal-scavenger agent or a combination thereof as defined herein.

In an optional aspect, the chromogenic solution may be prepared and tailored to the particular absorptive material.

In some implementations, releasing the chromogenic solution includes pouring the chromogenic solution under gravity onto the powder bed. In some implementations, pouring the chromogenic solution includes dripping the aqueous solution in the form of discrete drops onto the powder bed such that the agglomerated humid material is produced in the form of discrete humid particles.

It is understood that the implementations of the process described in the section "Process for manufacturing particles of water-absorbing material" can be applied to the manufacturing of the particles of chromogenic absorbent material.

EXAMPLES

Example 1

Experiments were performed by preparing particles of chromogenic absorbent material (i.e. particles of water-absorbing material) having different compositions and testing the particles when contacted with a blood-containing solution.

Particles of chromogenic absorbent material were prepared by mixing pregelatinized starch (PGS), microcrystalline cellulose (MCC) and sodium polyacrylate as the superabsorbent polymer (SAP), in powder form, thereby obtaining an absorptive powder mixture; The absorptive powder mixture was disposed onto a laboratory bench top to obtain a powder bed; the chromogenic solution was dripped onto the powder bed to obtain solution-impregnated humid particles; the solution-impregnated humid particles were maintained immobile on the bench top (i.e. in substantially shear-less conditions) for several seconds until the solution-impregnated humid particles agglomerated into stable agglomerated humid particles; and agglomerated humid particles were dried in an oven at 65° C. to obtain the particles of chromogenic absorbent material. In this case, the particles of chromogenic absorbent material were obtained in the form of granules having a length of between about 0.25 cm and about 0.75 cm.

The chromogenic solution I that was used is detailed in Table 1:

TABLE 1

| Compound | Molar mass (g/mol) | Mass or volume | Concentration (mmol/L) |
|---|---|---|---|
| Water (solvent) | — | 50 mL | — |
| Acetone (solvent) | — | 50 mL | — |
| TMB (chromogenic indicator) | 240.34 | 312 mg | 13 |
| CHP (oxidizing agent) | 152.19 | 114 mg | 7.5 |
| 4-lepidine (color enhancer) | 143.19 | 107 mg | 7.5 |
| Polyvinylpyrrolidone (stabilizer) | — | 30 mg | — |
| Ascorbic acid (stabilizer) | 176.12 | 20 mg | 1.15 |

The particles of chromogenic absorbent material were prepared with varying ratios of PGS/MCC and a varying amount of sodium polyacrylate-based SAP, and are numbered as shown in Table 2:

TABLE 2

| | 0 wt. % sodium polyacrylate | 1 wt. % sodium polyacrylate | 2 wt. % sodium polyacrylate | 3 wt. % sodium polyacrylate |
|---|---|---|---|---|
| 35% PGS/65% MCC | 1 | 2 | 3 | 4 |
| 40% PGS/60% MCC | 5 | 6 | 7 | 8 |
| 45% PGS/55% MCC | 9 | 10 | 11 | 12 |
| 55% PGS/45% MCC | 13 | 14 | 15 | 16 |
| 60% PGS/40% MCC | 17 | 18 | 19 | 20 |
| 65% PGS/35% MCC | 21 | 22 | 23 | 24 |

The particles of chromogenic absorbent material shown in Table 2 were placed on a bentonite-based litter and contacted with 5 mL of a 0.0215% blood solution or 5 mL of demineralized water which did not contain blood. Particles which were not contacted with any solution were also placed on the litter as a negative control.

FIGS. 3A, 3B, 3C and 3D illustrate samples as numbered in Table 2, and placed on a bentonite-based litter. In each figure, the top picture shows the granules 30 minutes after contact with the solutions, the middle picture shows the granules 2 hours after contact, and the bottom picture shown the granules 18 hours after contact. In each picture of each Figure, the top row of granules is the negative control; the middle row shows granules contacted with 5 mL of demineralized water which did not contain blood; and the bottom row shows granules contacted with 5 mL of a 0.0215% blood solution.

Figure 3A:
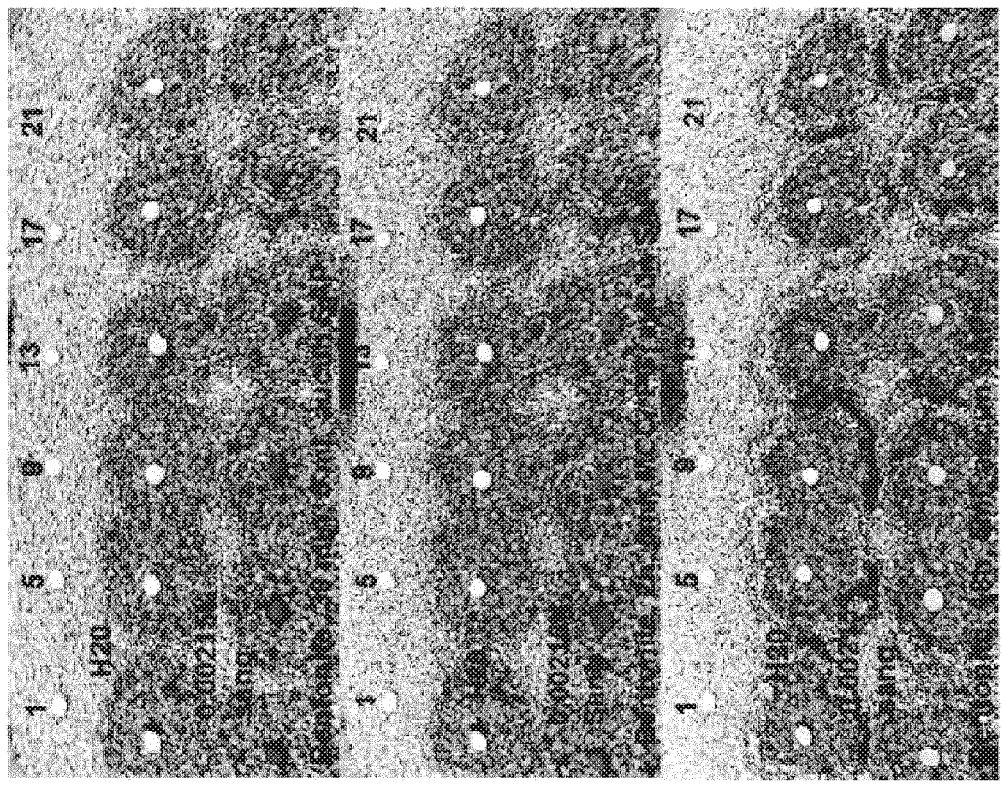
FIG. 3A shows photographs of six samples of particles of chromogenic absorbent materials after 30 minutes, 2 hours and 18 hours of contact with a diluted blood solution.

As can be seen in FIG. 3A, granules No. 1, 5, 9, 13, 17 and 21 were contacted with the different solutions (these granules contained 0 wt. % of superabsorbent polymer). The granules contacted with demineralized water did not change color and had the same white color as the negative control granules 30 mins, 2 h and 18 h after contact. The granules contacted with the blood solution had already turned blue 30 mins after contact. The blue coloration was distinctive. 2 h after contact, the blue coloration was still distinctive and present. 18 h after contact, the blue coloration had faded and the granules turned off-white or yellow. The blue coloration was present and distinctive for about 8 hours before fading.

Figure 3B:
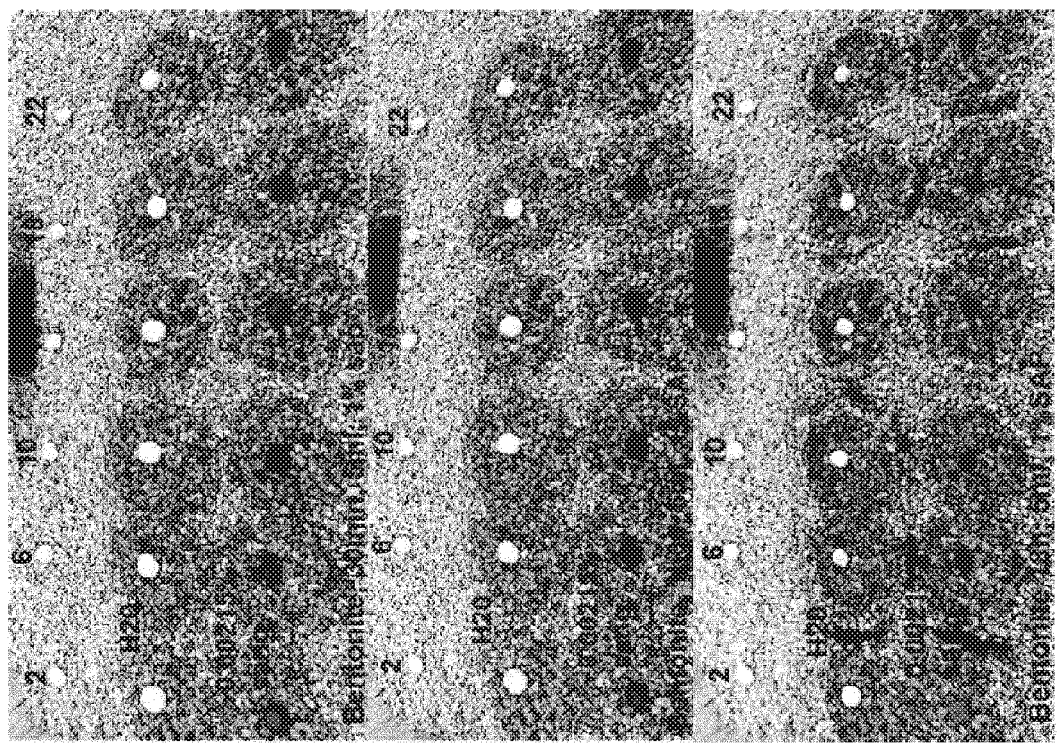
FIG. 3B shows photographs of six samples of particles of chromogenic absorbent materials including 1% of superabsorbent polymer after 30 minutes, 2 hours and 18 hours of contact with a diluted blood solution.

As can be seen in FIG. 3B, granules No. 2, 6, 10, 14, 18 and 22 were contacted with the different solutions (these granules contained about 1 wt. % of superabsorbent polymer). The granules contacted with demineralized water did not change color and had the same white color as the negative control granules 30 mins, 2 h and 18 h after contact. The granules contacted with the blood solution had already turned blue 30 mins after contact. The blue coloration was distinctive. 2 h after contact, the blue coloration was still distinctive and present. 18 h after contact, the blue coloration was still distinctive and present. The addition of 1 wt. % SAP had a positive effect on the retention of blue coloration in the granules after contact with a blood solution.

Figure 3C:
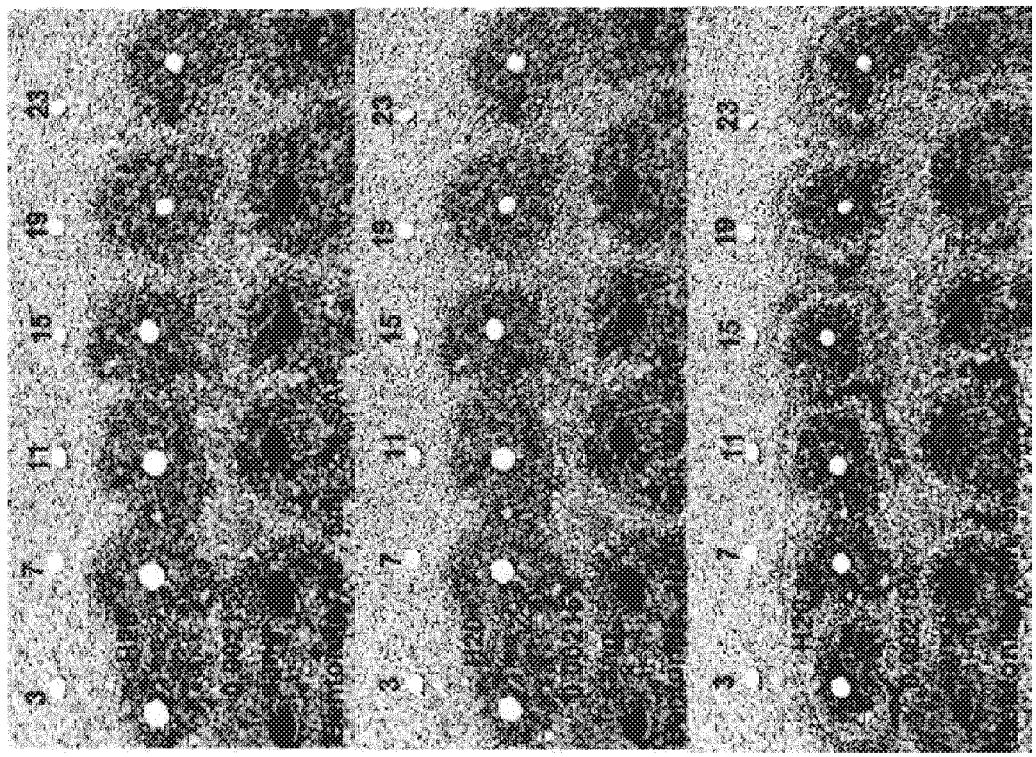
FIG. 3C shows photographs of six samples of particles of chromogenic absorbent materials including 2% of superabsorbent polymer after 30 minutes, 2 hours and 18 hours of contact with a diluted blood solution.

As can be seen in FIG. 3C, granules No. 3, 7, 11, 15, 19 and 24 were contacted with the different solutions (these granules contained about 2 wt. % of superabsorbent polymer). The same results as the ones observed and illustrated in FIG. 3B were obtained.

Figure 3D:
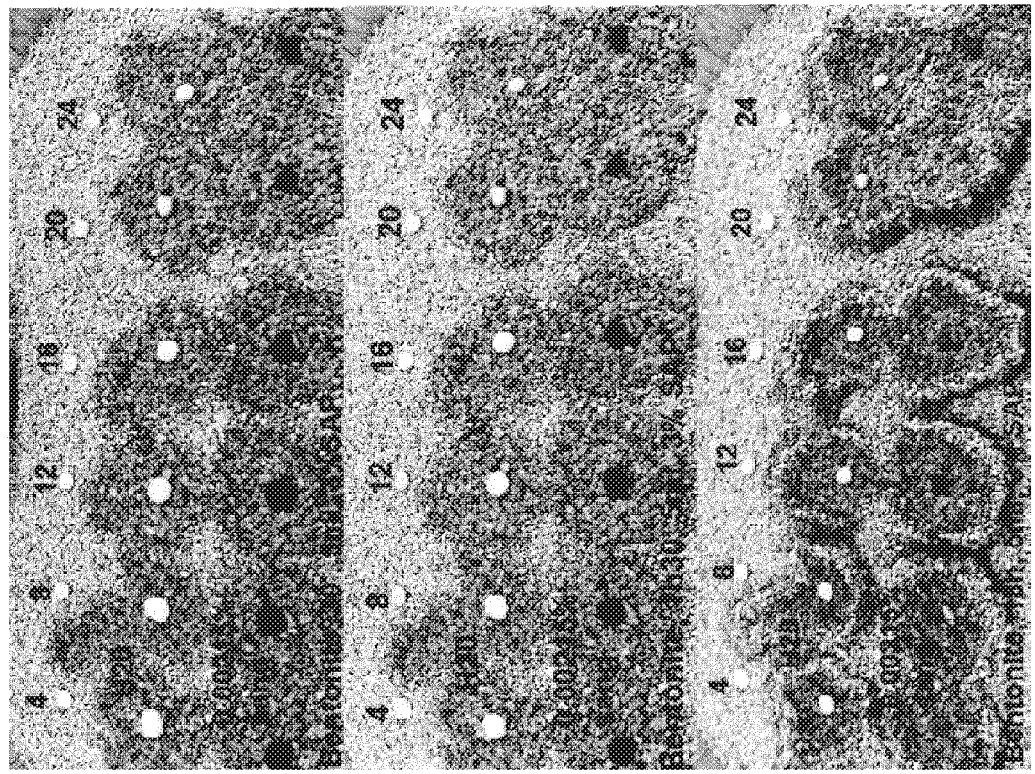
FIG. 3D shows photographs of six samples of particles of chromogenic absorbent materials including 3% of superabsorbent polymer after 30 minutes, 2 hours and 18 hours of contact with a diluted blood solution.

As can be seen in FIG. 3D, granules No. 4, 8, 12, 16, 20 and 25 were contacted with the different solutions (these granules contained about 3 wt. % of superabsorbent polymer). The same results as the ones observed and illustrated in FIGS. 3B and 3C were obtained.

Example 2

Experiments were performed by preparing particles of chromogenic absorbent material using different polysaccharides and mixtures thereof, and testing said particles when contacted with a blood-containing solution. The polysaccharides used in this Example were pregelatinized starch (PGS), microcrystalline cellulose (MCC) and carboxymethylcellulose (CMC).

The particles were prepared as described in Example 1. No superabsorbent polymer was used in this Example and the mixing step was not performed when only one polysaccharide was used. The same chromogenic solution I as described in Example 1 was also used.

Particles of chromogenic absorbent material were prepared using various polysaccharides and mixtures thereof, and are numbered as shown in Table 3.

TABLE 3

| Polysaccharide or polysaccharide mixture | Sample number |
| --- | --- |
| 50% PGS/ 50% MCC | 25 |
| 100% CMC | 26 |
| 100% PGS | 27 |

Figure 4:
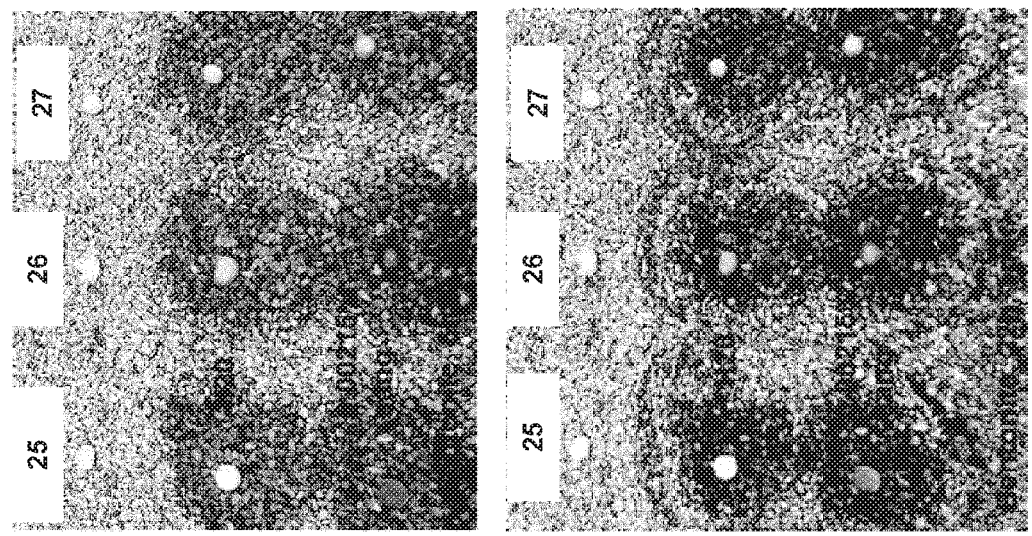
FIG. 4 shows photographs of three samples of particles of chromogenic absorbent materials including after 6 h 30 and 22 hours of contact with a diluted blood solution.

FIG. 4 shows the granules 6 h 30 and 22 h after contact with 5 mL of demineralized water which did not contain blood (middle row) or 5 mL of a 0.0215% blood solution (bottom row). The top row is the negative control showing granules which were not contacted with either solution. A deep blue coloration rapidly appeared a few minutes after contact with the blood-containing solution (not shown). The granules contacted with demineralized water stayed substantially white or became slightly yellow. After 6 h 30, samples No. 25 and 26 retained the deep blue coloration, while the blue coloration of sample No. 27 was lighter. After 22 h, sample No. 25 retained the deep blue coloration, sample No. 26 had a light blue coloration, and the coloration of sample No. 27 had substantially faded.

It is to be noted that all the samples prepared enable the detection of blood. Using 50% PGS/50% MCC as the absorptive material enabled the blue coloration to be retained for a longer period when compared with 100% CMC and 100% PGS granules.

Example 3

Experiments have been performed by preparing particles of chromogenic absorbent material using a mixture of 50% microcrystalline cellulose (MCC) and 50% carboxymethyl cellulose (CMC) as the absorptive material, and different chromogenic solutions. Said particles were contacted with glucose-containing solutions.

The composition of the chromogenic solution II is detailed in Table 4.

TABLE 4

| Solvents and compounds | Mass or volume |
| --- | --- |
| Water (solvent) | 50 mL |
| Acetone (solvent) | 50 mL |
| TMB (chromogenic indicator) | 312 mg |
| Glucose oxidase (first catalytic compound) | 6 mg |
| Horseradish peroxidase (second catalytic compound) | 5 mg |

Chromogenic solution II shown in Table 4 was diluted at ratios of 1:2 and 1:10 to obtain chromogenic solutions III (1:2 dilution) and IV (1:10 dilution).

Particles of chromogenic absorbent material were prepared by mixing carboxymethyl cellulose (CMC) and microcrystalline cellulose (MCC), thereby obtaining an absorptive powder mixture; The absorptive powder mixture was disposed onto a laboratory bench top to obtain powder beds; chromogenic solutions II, III or IV were dripped onto the powder beds to obtain solution-impregnated humid particles; the solution-impregnated humid particles were maintained immobile on the bench top (i.e. in substantially shear-less conditions) for several seconds until the solution-impregnated humid particles agglomerated into stable agglomerated humid particles; and the agglomerated humid particles were dried in an oven at 65° C. to obtain the particles of chromogenic absorbent material.

Figure 5:
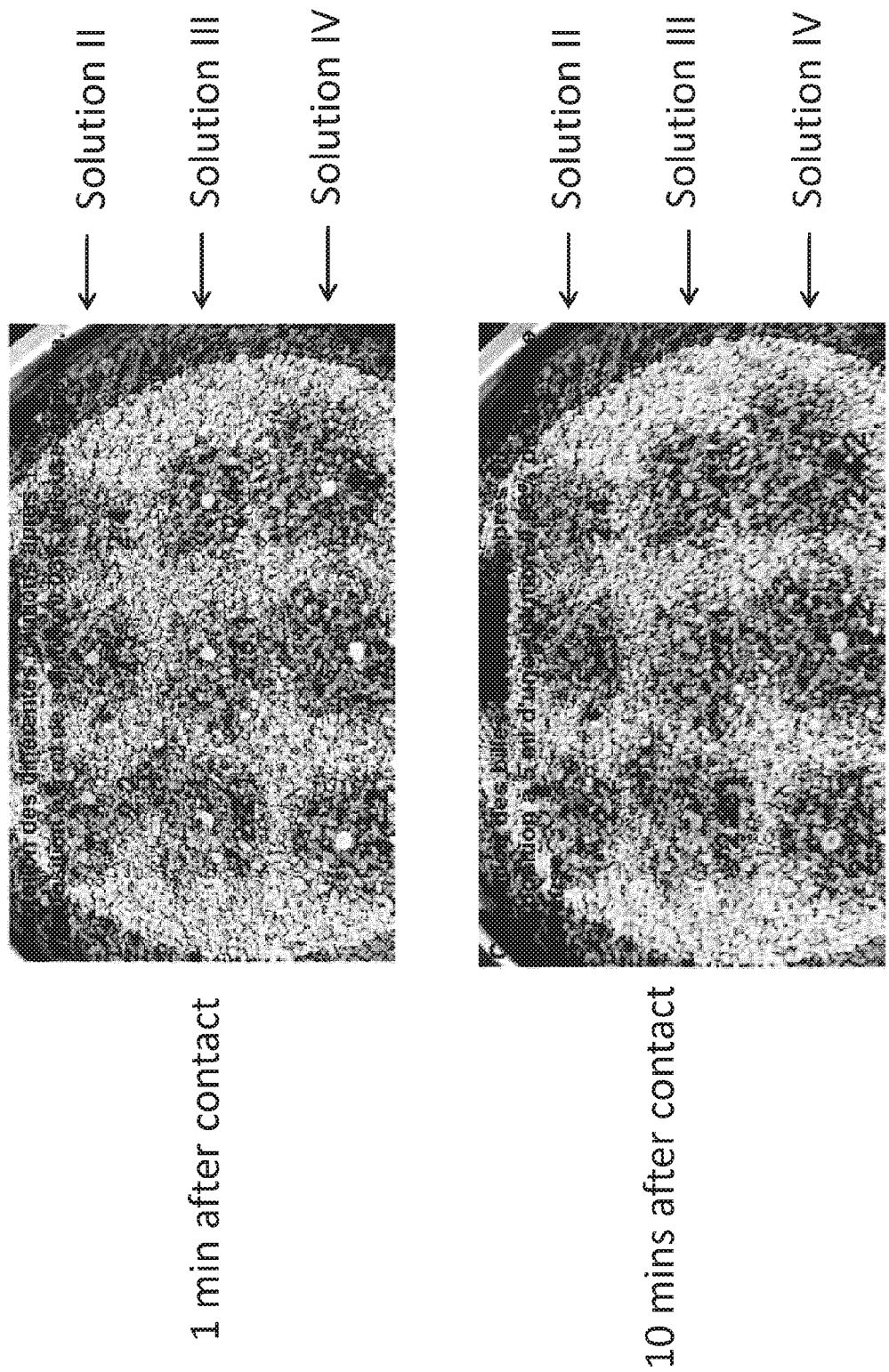
FIG. 5 shows photographs of samples of particles of chromogenic absorbent materials including after 1 minute and 10 minutes of contact with glucose solutions of different concentrations.

FIG. 5 shows particles of chromogenic absorbent material 1 minute (top picture) and 10 minutes (bottom picture) after contact with a solution containing 0.03% of glucose. In each picture, the top row corresponds to chromogenic absorbent material made with chromogenic solution II, the middle row corresponds to chromogenic absorbent material made with chromogenic solution III, and the bottom row corresponds to chromogenic absorbent material made with chromogenic solution IV. As can be seen, when the more concentrated solution II was used, the blue coloration is deeper and appears within 1 minute of contact. When the lower concentration solution IV is used, the deep blue coloration appeared within 10 minutes of contact.

Example 4

Experiments were also performed by measuring the free swelling capacity (FSC) of particles of chromogenic absorbent material. The particles of chromogenic absorbent material were prepared as described in Example 1 using PGS, Xanthan or guar as the water-absorbing polysaccharide, and MCC. The measurements were performed by soaking the samples in water for 30 minutes and draining the water remaining at the surface for 10 minutes. The values obtained were compared with the FSC values of particles obtained by extrusion or pressing. The results are detailed in Table 5.

TABLE 5

| Particle type | FSC % |
| --- | --- |
| Extruded starch granule without gas injection (comparative) | 190 |
| Extruded starch granule with gas injection (comparative) | 200 |
| Pressed paper pulp pellet (comparative) | 500 |
| 50% PGS/50% MCC granule (sample No. 25 of Example 2) | 1080 |
| 50% Xanthan/50% MCC granule | 3360 |
| 50% guar gum/50% MCC granule | 2030 |

The particles of chromogenic absorbent material made from PGS/MCC, xanthan/MCC and guar gum/MCC all exhibit high FSC values. This is indicative of a very high porosity and surprisingly high absorption properties when compared with the extruded starch granules and pressed paper pulp pellets known in the art.

Example 5

Experiments have also been performed by measuring the density of particles of chromogenic absorbent material. The particles of chromogenic absorbent material were prepared as described in Example 1 using PGS, Xanthan or guar as the water-absorbing polysaccharide, and MCC. The values obtained were compared with the density values of particles known in the art and obtained by extrusion or pressing. The results are detailed in Table 6.

TABLE 6

| Particle type | Density (g/cm$^3$) |
| --- | --- |
| Extruded starch granule without gas injection (comparative) | 0.60 |
| Extruded starch granule with gas injection (comparative) | 0.48 |
| Pressed paper pulp pellet (comparative) | 0.40 |
| 50% PGS/50% MCC granule (sample No. 25 of Example 2) | 0.33 |
| 50% Xanthan/50% MCC granule | 0.37 |
| 50% guar gum/50% MCC granule | 0.26 |

The particles of chromogenic absorbent material made from PGS/MCC, xanthan/MCC and guar gum/MCC exhibit lower density values when compared with the extruded starch granules and pressed paper pulp pellets known in the art.

Example 6

Experiments have been performed to obtain scanning electron micrographs of cross sections of particles of extruded starch with or without injected gas during extrusion (FIGS. 7A and 7B, comparative) and of a cross section of a particle of chromogenic absorbent material corresponding to sample 25 as shown in Example 2 (FIG. 7C). The images obtained were analyzed to determine the pore density and the equivalent diameter of the pores. Prior to imaging, the respective particles were first hardened by freezing in liquid nitrogen and cut in the frozen state. The scanning electron microscope used was a MEB JEOL JSM-5900LV™ (low vacuum).

The pore density and equivalent diameter measurements were performed by using the Nikon NIS-Elements D™ image analysis software. The results are detailed in Table 7.

TABLE 7

| Particle type | Pore density (%) | Equivalent diameter (μm) |
| --- | --- | --- |
| Extruded starch granule without gas injection (comparative) | 7.6 | 7.8 |
| Extruded starch granule with gas injection (comparative) | 10.8 | 11.5 |
| 50% PGS/50% MCC granule (sample No. 25 of Example 2) | 29.5 | 25.3 |

The particles of corresponding to sample No. 25 of Example 2 have a higher pore density and equivalent pore diameter than the particles of extruded starch (made with or without gas injection during high shear extrusion).

Example 7

Experiments have been performed on sample No. 25 of Example 2 to measure the total porosity and effective porosity of particles of chromogenic absorbent material. Comparative measurements were also performed on extruded starch granules (with or without injected gas during high shear extrusion). The porosity measurements were performed as follows.

200 mL of particles were placed in a container. The particles were weighed (mass m). Acetone was added to soak the particles and completely cover the particles with solvent. The volume of solvent required to cover all the particles was measured (Vc). The soaked particles were removed from the container and the volume of remaining solvent was measured (Vr). The volume of liquid absorbed by the chromogenic absorbent particles (Va=Vc−Vr) was calculated. The total porosity is then obtained by calculating the ratio of the volume of added liquid (Vc) to the volume of particles (V), and the effective porosity is calculated using Equation 2 detailed above. The results are summarized in Table 8.

TABLE 8

| Particle type | Mass of particles (g) | Vc (mL) | Va (mL) | Total porosity (%) | Effective porosity (mL/g) |
|---|---|---|---|---|---|
| Extruded starch granule without gas injection (comparative) | 120 | 104 | 18 | 52% | 0.15 |
| Extruded starch granule with gas injection (comparative) | 96 | 116 | 16 | 58% | 0.167 |
| 50% PGS/50% MCC granule (sample No. 25 of Example 2) | 66 | 150 | 65 | 75% | 0.985 |

As can be seen, the particles of chromogenic absorbent material made of 50% PGS and 50% MCC have an effective porosity which is substantially higher than extruded starch particles obtained with or without gas injection during high shear extrusion.

Example 8

Experiments were performed by preparing particles of chromogenic absorbent material (i.e. particles of water-absorbing material) using an absorptive powder mixture having the following composition: 49 wt % PGS; 49% MCC; and 2 wt % sodium polyacrylate (SAP).

The particles were prepared using a Bogen universal indicator solution detailed in table 9 below:

TABLE 9

| Components of the chromogenic solution (pH Indicator solution) | wt % |
|---|---|
| Water | 52.4 |
| Ethanol | 43 |
| 2-propanol | 2.4 |
| Methanol | 2.1 |
| Bromothymol blue (sodium salt) | 0.06 |
| Phenolphthalein | 0.06 |
| Methyl red | 0.02 |

Particles of chromogenic absorbent material were prepared by mixing pregelatinized starch (PGS), microcrystalline cellulose (MCC) and sodium polyacrylate as the superabsorbent polymer (SAP), in powder form, thereby obtaining the absorptive powder mixture; The absorptive powder mixture was disposed onto a laboratory bench top to obtain a powder bed; the chromogenic solution was dripped onto the powder bed to obtain solution-impregnated humid particles; the solution-impregnated humid particles were maintained immobile on the bench top (i.e. in substantially shear-less conditions) for several seconds until the solution-impregnated humid particles agglomerated into stable agglomerated humid particles; and agglomerated humid particles were dried in an oven at 65° C. to obtain the particles of chromogenic absorbent material. In this case, the particles of chromogenic absorbent material were obtained in the form of granules having a length of between about 0.25 cm and about 0.75 cm.

The particles were tested to measure the pH of various pH-controlled solutions, and the results are summarized in Table 10 below:

TABLE 10

| pH | Color |
|---|---|
| 4 | Red |
| 5 | Orange |
| 6 | Orange-yellow |
| 7 | Yellow-green |
| 8 | Green |
| 9 | Blue-green |
| 10 | Blue |

Example 9

Experiments were performed by preparing particles of chromogenic absorbent material (i.e. particles of water-absorbing material) having the compositions shown in Table 11, and using the process described in Example 1 and the chromogenic solution shown in Table 1.

TABLE 11

| No. | wt % MCC | wt % PGS | wt % SAP |
|---|---|---|---|
| 9.1 | 50 | 50 | 0 |
| 9.2 | 49 | 49 | 2 |
| 9.3 | 39 | 59 | 2 |
| 9.4 | 59 | 39 | 2 |
| 9.5 | 49 | 49 | 2 |

It is also noted that particles 9.5 and particles 9.2 have the same composition, but particles 9.5 have been further dried under vacuum after having been heat-dried. Particles 9.1 to 9.5 have a spheroidal shape. The hardness of particles 9.1 to 9.5 has been measured by applying axial and lateral compression forces such that the particles are compressed by 1 mm. The compression speed was of 10 mm/min from 0 mm of compression to 1.1 mm of compression. It is noteworthy that an "axial" compression corresponds to a compression in an axis coaxial to the axis of the dripping, and that a "lateral" is a compression in an axis perpendicular to the axis of the dripping.

The force necessary to compress the particles by 1 mm is shown in Table 12. The particles were also compressed by 1.1 mm and the % of particles which broke or were disaggregated is also shown in Table 12.

TABLE 12

| No. | Type of compression force | Force at 1 mm compression (N) | Mean weight of the particles (mg) | % of particles which break after 1.1 mm compression |
|---|---|---|---|---|
| 9.1 | axial | 57 ± 10 | 27.5 | 20% |
| 9.2 | axial | 74 ± 15 | 26.1 | 0% |
| 9.3 | axial | 82 ± 11 | 23.8 | 0% |
| 9.4 | axial | 26 ± 5 | 23.0 | 20% |
| 9.5 | axial | 84 ± 17 | 36.2 | 0% |
| 9.1 | Lateral | 25 ± 4 | 23.7 | 0% |
| 9.2 | Lateral | 25 ± 6 | 28.5 | 0% |
| 9.3 | Lateral | 38 ± 5 | 25.5 | 0% |
| 9.4 | Lateral | 14 ± 1 | 25.6 | 0% |
| 9.5 | Lateral | 35 ± 5 | 35.6 | 0% |

Example 10

Experiments were performed to assess the physical behavior of chromogenic particles when mixed with an animal litter. 1.5 g of Chromogenic particles 25 (described in Example 2) were mixed with a bed of animal litter particles provided in a container. The bed of animal litter particles had a thickness of about 1.5 inches. The mixing was performed such that the chromogenic particles were evenly distributed within the animal litter. The container was then shaken laterally to verify whether the chromogenic particles migrated to the surface of the bed of animal litter particles. Various types of animal litter were tested separately, including animal litter based on the following components:
bentonite;
montmorillonite;
attapulgite;
fine silica beads (Nullodor™);
coarse silica with blue crystals (President's Choice™);
ECO LIFE™; and
a paper-based litter (Daily Scoops™).

In all cases, the chromogenic particles 25 migrated to the surface.

When water was added to the animal litter, the chromogenic particles 25 expanded after absorbing the water, and still migrated to the surface of the animal litter.

Example 11

Experiments were performed by preparing particles of chromogenic absorbent material (i.e. particles of water-absorbing material) using the chromogenic solution V shown in Table 13, and testing the particles when contacted with a blood-containing solution.

Particles of chromogenic absorbent material were prepared by mixing PGS (49 wt %), MCC (49 wt %) and sodium polyacrylate (2 wt %), in powder form, thereby obtaining an absorptive powder mixture; The absorptive powder mixture was disposed onto a laboratory bench top to obtain a powder bed; the chromogenic solution was dripped onto the powder bed to obtain solution-impregnated humid particles; the solution-impregnated humid particles were maintained immobile on the bench top (i.e. in substantially shear-less conditions) for several seconds until the solution-impregnated humid particles agglomerated into stable agglomerated humid particles; and agglomerated humid particles were dried in an oven at 65° C. to obtain the particles of chromogenic absorbent material. In this case, the particles of chromogenic absorbent material were obtained in the form of granules having a length of between about 0.25 cm and about 0.75 cm. The granules were formed by dripping the solution V on the absorptive powder mixture with a solution:powder ratio of 1:1 (v/w).

The chromogenic solution V that was used is detailed in Table 13:

TABLE 13

| Compound | % w/w |
|---|---|
| Water (solvent) | 54.86 |
| Acetone (solvent) | 43.89 |
| TMB (chromogenic indicator) | 0.34 |
| CHP (oxidizing agent) | 0.43 |
| 4-lepidine (color enhancer) | 0.24 |
| 6-Methoxyquinoline (stabilizer) | 0.17 |
| EDTA (free acid 0.5 M—metal scavenger agent) | 0.06 |
| BHT (stabilizer) | 0.01 |

The chromogenic absorbent particles made with chromogenic solution V were used for detecting traces of blood in excretions having a pH of 8 or greater and/or containing proteins.

The invention claimed is:

1. A process for manufacturing a chromogenic absorbent material for detecting glucose in an animal excretion, the process comprising:
   providing an absorptive powder comprising a water-absorbing polysaccharide onto a surface, thereby obtaining a powder bed;
   releasing a chromogenic solution from a solution dispenser so as to contact the powder bed, thereby forming a solution-impregnated humid material, the chromogenic solution comprising:
      an oxido-reductase;
      a peroxidase or pseudoperoxidase; and
      a chromogenic indicator oxidizable into a colored and/or fluorescent substance in the presence of the oxido-reductase, the peroxidase or pseudoperoxidase and glucose;
   maintaining the solution-impregnated humid material supported by the surface and in substantially shear-less conditions until the solution-impregnated humid material agglomerates to produce an agglomerated humid material; and
   drying the agglomerated humid material, thereby forming the chromogenic absorbent material, the chromogenic absorbent material having a density of about 0.20 g/cm$^3$ to about 0.39 g/cm$^3$,
   wherein the absorptive powder is unreactive to the oxido-reductase.

2. The process of claim 1, wherein releasing the aqueous solution comprises pouring the aqueous solution under gravity onto the powder bed.

3. The process of claim 1, wherein the step of releasing the aqueous solution is performed such that a first portion of the absorptive powder is used to form the agglomerated humid material and a second portion of the absorptive powder remains as residual powder.

4. The process of claim 3, further comprising separating the residual powder from the agglomerated humid material.

5. The process of claim 4, wherein separating the residual powder from the agglomerated humid material comprises sieving.

6. The process of claim 3, further comprising recycling at least a portion of the residual powder for re-use as part of the powder bed.

7. The process of claim 1, further comprising controlling a thickness of the powder bed between about 1 cm and about 5 cm.

8. The process of claim 1, wherein the water-absorbing polysaccharide comprises a cellulose derivative, an alginate, an alginate derivative, a gelling polysaccharide or a mixture thereof.

9. The process of claim 1, wherein the water-absorbing polysaccharide comprises carboxymethyl cellulose (CMC).

10. The process of claim 1, wherein the absorptive powder further comprises a second polysaccharide mixed with the water-absorbing polysaccharide.

11. The process of claim 10, wherein the second polysaccharide comprises microcrystalline cellulose (MCC), nanocrystalline cellulose (NCC), or a mixture thereof.

12. The process of claim 1, wherein the absorptive powder comprises carboxymethyl cellulose (CMC) and microcrystalline cellulose (MCC).

13. The process of claim 1, wherein the drying comprises at least one of drying under vacuum and drying by heating.

14. The process of claim 1, wherein the aqueous solution is released in the form of discrete drops onto the powder bed.

15. The process of claim 1, wherein:
the oxido-reductase comprises glucose oxidase;
the peroxidase or pseudoperoxidase comprises horseradish peroxidase; and
the chromogenic indicator comprises a benzidine-type compound.

16. The process of claim 1, wherein the chromogenic absorbent material has an effective porosity of about 0.5 mL/g to about 2.0 mL/g.

17. The process of claim 1, wherein the chromogenic absorbent material has a free swelling capacity greater than about 900%.

18. The process of claim 10, wherein the second polysaccharide comprises cellulose.

19. The process of claim 1, wherein the water-absorbing polysaccharide comprises at least one of pregelatinized starch, a cellulose ester and a cellulose ether.

20. The process of claim 19, wherein the absorptive powder further comprises cellulose.

* * * * *